(12) United States Patent
Baker et al.

(10) Patent No.: US 7,541,439 B2
(45) Date of Patent: Jun. 2, 2009

(54) THROMBOPOIETIN PROTEINS WITH IMPROVED PROPERTIES

(75) Inventors: Matthew Baker, Cambridge (GB); John Watkins, Cambridge (GB)

(73) Assignee: Merck Patent GmbH, Darmstadt (DE)

( * ) Notice: Subject to any disclaimer, the term of this patent is extended or adjusted under 35 U.S.C. 154(b) by 377 days.

(21) Appl. No.: 10/561,097

(22) PCT Filed: Jun. 25, 2004

(86) PCT No.: PCT/EP2004/006887

§ 371 (c)(1),
(2), (4) Date: Dec. 16, 2005

(87) PCT Pub. No.: WO2005/000891

PCT Pub. Date: Jan. 6, 2005

(65) Prior Publication Data

US 2006/0160995 A1    Jul. 20, 2006

(30) Foreign Application Priority Data

Jun. 26, 2003   (EP)   ................................. 03014331

(51) Int. Cl.
*C07K 19/00*  (2006.01)
*C07K 14/52*  (2006.01)
*A61K 38/19*  (2006.01)

*C12N 15/19*  (2006.01)

(52) U.S. Cl. .................. 530/387.3; 530/351; 435/69.5; 424/198.1; 424/192.1

(58) Field of Classification Search ....................... None
See application file for complete search history.

(56) References Cited

U.S. PATENT DOCUMENTS

| | | | | |
|---|---|---|---|---|
| 5,879,673 | A | * | 3/1999 | Thomas .................... 424/85.1 |
| 6,238,890 | B1 | * | 5/2001 | Boime et al. ............... 435/69.7 |
| 7,101,674 | B2 | * | 9/2006 | Le et al. ..................... 435/7.1 |
| 7,122,634 | B2 | * | 10/2006 | Lollar ........................ 530/383 |
| 7,186,804 | B2 | * | 3/2007 | Gillies et al. ............... 530/351 |

OTHER PUBLICATIONS

Park et al., JBC 173(1):256-61, 1998.*

* cited by examiner

*Primary Examiner*—Lorraine Spector
(74) *Attorney, Agent, or Firm*—Olson & Cepuritis, Ltd.

(57) ABSTRACT

The invention concerns human thrombopoietin and in particular modified forms of thrombopoietin (TPO) with improved properties. The improved proteins contain amino acid substitutions at specific positions within the TPO molecule. The invention provides modified TPO molecules, preferably fusion proteins comprising immunoglobulin constant regions and modified human TPO, with improved biological activity concomitant with reduced immunogenic potential in the protein. The improved proteins are intended for therapeutic use in the treatment of diseases in humans.

6 Claims, 6 Drawing Sheets

(A)

(B)

SPAPPACDLRVL SKLLRDSHVLHS RLSQCPEVHPLP TPVLLPAVDFSL

```
Region 1

GEWKTQMEETKA QDILGAVTLLLE GVMAARGQLGPT CLSSLLGQLSGQ
49
```

VRLLLGALQSLL GTQLPPQGRTTA HKDPNAIFLSFQ HLLRGKVRFLML
97

```
                        Region 2

VGGSTLCVRRAP  PTTAVPSRTSLV LTLNEL
145                                 174
```

(A)

(B)

SEQUENCE LISTING

<160> NUMBER OF SEQ ID NOS: 138

<210> SEQ ID NO 1
<211> LENGTH: 174
<212> TYPE: PRT
<213> ORGANISM: Artificial Sequence
<220> FEATURE:
<223> OTHER INFORMATION: Modified human TPO
<220> FEATURE:
<221> NAME/KEY: VARIANT
<222> LOCATION: 50, 51, 55, 58
<223> OTHER INFORMATION: X=A or E;
      X=S or W;
      X=A, T, K, S or M;
      X=A or T
<220> FEATURE:
<221> NAME/KEY: VARIANT
<222> LOCATION: 60, 61, 63, 67

```
<223> OTHER INFORMATION: X=R or A;
      X=A, T or Q;
      X=A, T, or I;
      X=A, T or V
<220> FEATURE:
<221> NAME/KEY: VARIANT
<222> LOCATION: 69, 71, 72, 161
<223> OTHER INFORMATION: X=A, T, S or L;
      X=A or L;
      X=A, S or E;
      X=N, A, T, R, E, D, G, H, P, K, Q or V
<220> FEATURE:
<221> NAME/KEY: VARIANT
<222> LOCATION: 162
<223> OTHER INFORMATION: X=A or P

<400> SEQUENCE: 1

Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Xaa Xaa Lys Thr Gln Xaa Glu Glu Xaa Lys Xaa Xaa Asp Xaa Leu
 50                  55                  60

Gly Ala Xaa Thr Xaa Leu Xaa Xaa Gly Val Met Ala Ala Arg Gly Gln
65                  70                  75                  80

Leu Gly Pro Thr Cys Leu Ser Ser Leu Leu Gly Gln Leu Ser Gly Gln
             85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Xaa Xaa Ser Arg Thr Ser Leu Val Leu Thr Leu Asn Glu Leu
                165                 170

<210> SEQ ID NO 2
<211> LENGTH: 27
<212> TYPE: PRT
<213> ORGANISM: homo sapiens

<400> SEQUENCE: 2

Gly Glu Trp Lys Thr Gln Met Glu Glu Thr Lys Ala Gln Asp Ile Leu
  1               5                  10                  15

Gly Ala Val Thr Leu Leu Leu Glu Gly Val Met
             20                  25

<210> SEQ ID NO 3
<211> LENGTH: 15
<212> TYPE: PRT
<213> ORGANISM: homo sapiens

<400> SEQUENCE: 3

Pro Thr Thr Ala Val Pro Ser Arg Thr Ser Leu Val Leu Thr Leu
  1               5                  10                  15

<210> SEQ ID NO 4
<211> LENGTH: 332
```

```
<212> TYPE: PRT
<213> ORGANISM: homo sapiens

<400> SEQUENCE: 4

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
                35                  40                  45

Gly Glu Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Trp Gln Gln Gly Phe Arg Ala Lys Ile
                195                 200                 205

Pro Gly Leu Leu Asn Gln Thr Ser Arg Ser Leu Asp Gln Ile Pro Gly
                210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
                260                 265                 270

Pro Ser Pro Thr His Pro Pro Thr Gly Gln Tyr Thr Leu Phe Pro Leu
                275                 280                 285

Pro Pro Thr Leu Pro Thr Pro Val Val Gln Leu His Pro Leu Leu Pro
                290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330

<210> SEQ ID NO 5
<211> LENGTH: 7
<212> TYPE: PRT
<213> ORGANISM: Artificial Sequence
<220> FEATURE:
<223> OTHER INFORMATION: Linker peptide

<400> SEQUENCE: 5

Gly Ser Gly Ser Gly Ser Gly
```

-continued

```
<210> SEQ ID NO 6
<211> LENGTH: 174
<212> TYPE: PRT
<213> ORGANISM: Artificial Sequence
<220> FEATURE:
<223> OTHER INFORMATION: Modified human TPO

<400> SEQUENCE: 6

Ser Pro Ala Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Glu Trp Lys Thr Gln Met Glu Glu Thr Lys Arg Gln Asp Ile Leu
     50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 7
<211> LENGTH: 174
<212> TYPE: PRT
<213> ORGANISM: Artificial Sequence
<220> FEATURE:
<223> OTHER INFORMATION: Modified human TPO

<400> SEQUENCE: 7

Ser Pro Ala Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Glu Trp Lys Thr Gln Met Glu Glu Thr Lys Ala Gln Asp Ala Leu
     50                  55                  60

Gly Ala Thr Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125
```

```
Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Asn Ala Ser Arg Thr Ser Leu Val Leu Thr Leu Asn Glu Leu
                165                 170

<210> SEQ ID NO 8
<211> LENGTH: 174
<212> TYPE: PRT
<213> ORGANISM: Artificial Sequence
<220> FEATURE:
<223> OTHER INFORMATION: Modified human TPO

<400> SEQUENCE: 8

Ser Pro Ala Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Thr Leu
 50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Asn Ala Ser Arg Thr Ser Leu Val Leu Thr Leu Asn Glu Leu
                165                 170

<210> SEQ ID NO 9
<211> LENGTH: 174
<212> TYPE: PRT
<213> ORGANISM: Artificial Sequence
<220> FEATURE:
<223> OTHER INFORMATION: Modified human TPO

<400> SEQUENCE: 9

Ser Pro Ala Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Ala Glu Glu Thr Lys Ala Gln Asp Ala Leu
 50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95
```

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 10
<211> LENGTH: 174
<212> TYPE: PRT
<213> ORGANISM: Artificial Sequence
<220> FEATURE:
<223> OTHER INFORMATION: Modified human TPO

<400> SEQUENCE: 10

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Thr Glu Glu Thr Lys Ala Gln Asp Ala Leu
    50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 11
<211> LENGTH: 174
<212> TYPE: PRT
<213> ORGANISM: Artificial Sequence
<220> FEATURE:
<223> OTHER INFORMATION: Modified human TPO

<400> SEQUENCE: 11

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Thr Glu Glu Thr Lys Ala Gln Asp Thr Leu

```
                50                  55                  60
Gly Ala Ala Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 12
<211> LENGTH: 174
<212> TYPE: PRT
<213> ORGANISM: Artificial Sequence
<220> FEATURE:
<223> OTHER INFORMATION: Modified human TPO

<400> SEQUENCE: 12

Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
                35                  40                  45

Gly Glu Trp Lys Thr Gln Met Glu Glu Thr Lys Ala Ala Asp Ala Leu
     50                  55                  60

Gly Ala Ala Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 13
<211> LENGTH: 174
<212> TYPE: PRT
<213> ORGANISM: Artificial Sequence
<220> FEATURE:
<223> OTHER INFORMATION: Modified human TPO

<400> SEQUENCE: 13

Ser Pro Ala Pro Pro Ala Cys Asp Leu Arg Val Leu Ser Lys Leu Leu
 1               5                  10                  15
```

-continued

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Ala Asp Thr Leu
 50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
                165                 170

<210> SEQ ID NO 14
<211> LENGTH: 174
<212> TYPE: PRT
<213> ORGANISM: Artificial Sequence
<220> FEATURE:
<223> OTHER INFORMATION: Modified human TPO

<400> SEQUENCE: 14

Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Thr Leu
 50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
                165                 170

<210> SEQ ID NO 15
<211> LENGTH: 174
<212> TYPE: PRT
<213> ORGANISM: Artificial Sequence
<220> FEATURE:

<223> OTHER INFORMATION: Modified human TPO

<400> SEQUENCE: 15

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Thr Leu
 50                  55                  60

Gly Ala Ala Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170
```

<210> SEQ ID NO 16
<211> LENGTH: 174
<212> TYPE: PRT
<213> ORGANISM: Artificial Sequence
<220> FEATURE:
<223> OTHER INFORMATION: Modified human TPO

<400> SEQUENCE: 16

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ala Leu
 50                  55                  60

Gly Ala Ala Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170
```

<210> SEQ ID NO 17
<211> LENGTH: 174
<212> TYPE: PRT
<213> ORGANISM: Artificial Sequence
<220> FEATURE:
<223> OTHER INFORMATION: Modified human TPO

<400> SEQUENCE: 17

```
Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ala Leu
    50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
                165                 170
```

<210> SEQ ID NO 18
<211> LENGTH: 174
<212> TYPE: PRT
<213> ORGANISM: Artificial Sequence
<220> FEATURE:
<223> OTHER INFORMATION: Modified human TPO

<400> SEQUENCE: 18

```
Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ala Leu
    50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
```

```
                130              135              140
Val Gly Gly Ser Thr Leu Cys Val Arg Arg Ala Pro Pro Thr Thr Ala
145                  150                  155                  160

Thr Pro Ser Arg Thr Ser Leu Val Leu Thr Leu Asn Glu Leu
                165                  170

<210> SEQ ID NO 19
<211> LENGTH: 174
<212> TYPE: PRT
<213> ORGANISM: Artificial Sequence
<220> FEATURE:
<223> OTHER INFORMATION: Modified human TPO

<400> SEQUENCE: 19

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Arg Pro Ser Arg Thr Ser Leu Val Leu Thr Leu Asn Glu Leu
                165                 170

<210> SEQ ID NO 20
<211> LENGTH: 174
<212> TYPE: PRT
<213> ORGANISM: Artificial Sequence
<220> FEATURE:
<223> OTHER INFORMATION: Modified human TPO

<400> SEQUENCE: 20

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Met Gln Met Glu Glu Thr Lys Ala Gln Asp Ile Leu
50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95
```

```
Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
                165                 170

<210> SEQ ID NO 21
<211> LENGTH: 174
<212> TYPE: PRT
<213> ORGANISM: Artificial Sequence
<220> FEATURE:
<223> OTHER INFORMATION: Modified human TPO

<400> SEQUENCE: 21

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Thr Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 22
<211> LENGTH: 174
<212> TYPE: PRT
<213> ORGANISM: Artificial Sequence
<220> FEATURE:
<223> OTHER INFORMATION: Modified human TPO

<400> SEQUENCE: 22

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60
```

```
Gly Ala Thr Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
                165                 170

<210> SEQ ID NO 23
<211> LENGTH: 174
<212> TYPE: PRT
<213> ORGANISM: Artificial Sequence
<220> FEATURE:
<223> OTHER INFORMATION: Modified human TPO

<400> SEQUENCE: 23

Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Glu Trp Lys Thr Gln Met Glu Glu Thr Lys Ala Gln Asp Ile Leu
     50                  55                  60

Gly Ala Ala Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 24
<211> LENGTH: 174
<212> TYPE: PRT
<213> ORGANISM: Artificial Sequence
<220> FEATURE:
<223> OTHER INFORMATION: Modified human TPO

<400> SEQUENCE: 24

Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
```

```
                    20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
 50                  55                  60

Gly Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Glu Pro Ser Arg Thr Ser Leu Val Leu Thr Leu Asn Glu Leu
                165                 170

<210> SEQ ID NO 25
<211> LENGTH: 174
<212> TYPE: PRT
<213> ORGANISM: Artificial Sequence
<220> FEATURE:
<223> OTHER INFORMATION: Modified human TPO

<400> SEQUENCE: 25

Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Thr Leu
 50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
                165                 170

<210> SEQ ID NO 26
<211> LENGTH: 174
<212> TYPE: PRT
<213> ORGANISM: Artificial Sequence
<220> FEATURE:
<223> OTHER INFORMATION: Modified human TPO
```

<400> SEQUENCE: 26

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Thr Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Arg Pro Ser Arg Thr Ser Leu Val Leu Thr Leu Asn Glu Leu
                165                 170
```

<210> SEQ ID NO 27
<211> LENGTH: 174
<212> TYPE: PRT
<213> ORGANISM: Artificial Sequence
<220> FEATURE:
<223> OTHER INFORMATION: Modified human TPO

<400> SEQUENCE: 27

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Thr Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Glu Pro Ser Arg Thr Ser Leu Val Leu Thr Leu Asn Glu Leu
                165                 170
```

<210> SEQ ID NO 28
<211> LENGTH: 174
<212> TYPE: PRT
<213> ORGANISM: Artificial Sequence
<220> FEATURE:
<223> OTHER INFORMATION: Modified human TPO

<400> SEQUENCE: 28

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Thr Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 29
<211> LENGTH: 174
<212> TYPE: PRT
<213> ORGANISM: Artificial Sequence
<220> FEATURE:
<223> OTHER INFORMATION: Modified human TPO

<400> SEQUENCE: 29

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ala Leu
50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

```
Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 30
<211> LENGTH: 174
<212> TYPE: PRT
<213> ORGANISM: Artificial Sequence
<220> FEATURE:
<223> OTHER INFORMATION: Modified human TPO

<400> SEQUENCE: 30

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ala Leu
50                  55                  60

Gly Ala Thr Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 31
<211> LENGTH: 174
<212> TYPE: PRT
<213> ORGANISM: Artificial Sequence
<220> FEATURE:
<223> OTHER INFORMATION: Modified human TPO

<400> SEQUENCE: 31

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Thr Leu
50                  55                  60

Gly Ala Ala Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
```

-continued

```
                  100                 105                 110
Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 32
<211> LENGTH: 174
<212> TYPE: PRT
<213> ORGANISM: Artificial Sequence
<220> FEATURE:
<223> OTHER INFORMATION: Modified human TPO

<400> SEQUENCE: 32

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ala Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 33
<211> LENGTH: 174
<212> TYPE: PRT
<213> ORGANISM: Artificial Sequence
<220> FEATURE:
<223> OTHER INFORMATION: Modified human TPO

<400> SEQUENCE: 33

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ala Leu
    50                  55                  60
```

```
Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Glu Pro Ser Arg Thr Ser Leu Val Leu Thr Leu Asn Glu Leu
                165                 170

<210> SEQ ID NO 34
<211> LENGTH: 174
<212> TYPE: PRT
<213> ORGANISM: Artificial Sequence
<220> FEATURE:
<223> OTHER INFORMATION: Modified human TPO

<400> SEQUENCE: 34

Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
                 20                  25                  30

His Pro Leu Pro Thr Pro Val Leu Leu Pro Ala Val Asp Phe Ser Leu
             35                  40                  45

Gly Glu Trp Lys Thr Gln Met Glu Glu Thr Lys Ala Gln Asp Ala Leu
     50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Arg Pro Ser Arg Thr Ser Leu Val Leu Thr Leu Asn Glu Leu
                165                 170

<210> SEQ ID NO 35
<211> LENGTH: 174
<212> TYPE: PRT
<213> ORGANISM: Artificial Sequence
<220> FEATURE:
<223> OTHER INFORMATION: Modified human TPO

<400> SEQUENCE: 35

Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
                 20                  25                  30
```

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ala Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
            165                 170

<210> SEQ ID NO 36
<211> LENGTH: 174
<212> TYPE: PRT
<213> ORGANISM: Artificial Sequence
<220> FEATURE:
<223> OTHER INFORMATION: Modified human TPO

<400> SEQUENCE: 36

Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
            35                  40                  45

Gly Ala Trp Lys Thr Gln Met Glu Glu Thr Lys Ala Gln Asp Ile Leu
 50                  55                  60

Gly Ala Thr Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
            165                 170

<210> SEQ ID NO 37
<211> LENGTH: 174
<212> TYPE: PRT
<213> ORGANISM: Artificial Sequence
<220> FEATURE:
<223> OTHER INFORMATION: Modified human TPO

<400> SEQUENCE: 37

```
Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Ala Trp Lys Thr Gln Met Glu Glu Thr Lys Ala Gln Asp Ala Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170
```

<210> SEQ ID NO 38
<211> LENGTH: 174
<212> TYPE: PRT
<213> ORGANISM: Artificial Sequence
<220> FEATURE:
<223> OTHER INFORMATION: Modified human TPO

<400> SEQUENCE: 38

```
Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Ala Trp Lys Thr Gln Met Glu Glu Thr Lys Ala Gln Asp Thr Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170
```

<210> SEQ ID NO 39
<211> LENGTH: 174
<212> TYPE: PRT
<213> ORGANISM: Artificial Sequence
<220> FEATURE:
<223> OTHER INFORMATION: Modified human TPO

<400> SEQUENCE: 39

```
Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Ala Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Glu Pro Ser Arg Thr Ser Leu Val Leu Thr Leu Asn Glu Leu
                165                 170
```

<210> SEQ ID NO 40
<211> LENGTH: 174
<212> TYPE: PRT
<213> ORGANISM: Artificial Sequence
<220> FEATURE:
<223> OTHER INFORMATION: Modified human TPO

<400> SEQUENCE: 40

```
Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
    130                 135                 140
```

```
Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170
```

<210> SEQ ID NO 41
<211> LENGTH: 174
<212> TYPE: PRT
<213> ORGANISM: Artificial Sequence
<220> FEATURE:
<223> OTHER INFORMATION: Modified human TPO

<400> SEQUENCE: 41

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Asp Pro Ser Arg Thr Ser Leu Val Leu Thr Leu Asn Glu Leu
                165                 170
```

<210> SEQ ID NO 42
<211> LENGTH: 174
<212> TYPE: PRT
<213> ORGANISM: Artificial Sequence
<220> FEATURE:
<223> OTHER INFORMATION: Modified human TPO

<400> SEQUENCE: 42

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110
```

```
Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Glu Pro Ser Arg Thr Ser Leu Val Leu Thr Leu Asn Glu Leu
                165                 170

<210> SEQ ID NO 43
<211> LENGTH: 174
<212> TYPE: PRT
<213> ORGANISM: Artificial Sequence
<220> FEATURE:
<223> OTHER INFORMATION: Modified human TPO

<400> SEQUENCE: 43

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Gly Pro Ser Arg Thr Ser Leu Val Leu Thr Leu Asn Glu Leu
                165                 170

<210> SEQ ID NO 44
<211> LENGTH: 174
<212> TYPE: PRT
<213> ORGANISM: Artificial Sequence
<220> FEATURE:
<223> OTHER INFORMATION: Modified human TPO

<400> SEQUENCE: 44

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
```

```
                65                  70                  75                  80
Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
                130                 135                 140

Val Gly Gly Ser Thr Leu Cys Val Arg Arg Ala Pro Pro Thr Thr Ala
145                 150                 155                 160

His Pro Ser Arg Thr Ser Leu Val Leu Thr Leu Asn Glu Leu
                165                 170

<210> SEQ ID NO 45
<211> LENGTH: 174
<212> TYPE: PRT
<213> ORGANISM: Artificial Sequence
<220> FEATURE:
<223> OTHER INFORMATION: Modified human TPO

<400> SEQUENCE: 45

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
                35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
                130                 135                 140

Val Gly Gly Ser Thr Leu Cys Val Arg Arg Ala Pro Pro Thr Thr Ala
145                 150                 155                 160

Asn Pro Ser Arg Thr Ser Leu Val Leu Thr Leu Asn Glu Leu
                165                 170

<210> SEQ ID NO 46
<211> LENGTH: 174
<212> TYPE: PRT
<213> ORGANISM: Artificial Sequence
<220> FEATURE:
<223> OTHER INFORMATION: Modified human TPO

<400> SEQUENCE: 46

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30
```

```
His Pro Leu Pro Thr Pro Val Leu Pro Ala Val Asp Phe Ser Leu
            35                  40                  45

Gly Glu Trp Lys Thr Gln Met Glu Glu Thr Lys Ala Gln Asp Ile Leu
 50                      55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Pro Pro Ser Arg Thr Ser Leu Val Leu Thr Leu Asn Glu Leu
                165                 170
```

<210> SEQ ID NO 47
<211> LENGTH: 174
<212> TYPE: PRT
<213> ORGANISM: Artificial Sequence
<220> FEATURE:
<223> OTHER INFORMATION: Modified human TPO

<400> SEQUENCE: 47

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
 50                      55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Lys Pro Ser Arg Thr Ser Leu Val Leu Thr Leu Asn Glu Leu
                165                 170
```

<210> SEQ ID NO 48
<211> LENGTH: 174
<212> TYPE: PRT
<213> ORGANISM: Artificial Sequence
<220> FEATURE:
<223> OTHER INFORMATION: Modified human TPO

<400> SEQUENCE: 48

```
Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Gln Pro Ser Arg Thr Ser Leu Val Leu Thr Leu Asn Glu Leu
                165                 170

<210> SEQ ID NO 49
<211> LENGTH: 174
<212> TYPE: PRT
<213> ORGANISM: Artificial Sequence
<220> FEATURE:
<223> OTHER INFORMATION: Modified human TPO

<400> SEQUENCE: 49

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Arg Pro Ser Arg Thr Ser Leu Val Leu Thr Leu Asn Glu Leu
                165                 170

<210> SEQ ID NO 50
```

```
<211> LENGTH: 174
<212> TYPE: PRT
<213> ORGANISM: Artificial Sequence
<220> FEATURE:
<223> OTHER INFORMATION: Modified human TPO

<400> SEQUENCE: 50

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                 20                  25                  30

His Pro Leu Pro Thr Pro Val Leu Leu Pro Ala Val Asp Phe Ser Leu
             35                  40                  45

Gly Glu Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Thr Pro Ser Arg Thr Ser Leu Val Leu Thr Leu Asn Glu Leu
                165                 170

<210> SEQ ID NO 51
<211> LENGTH: 174
<212> TYPE: PRT
<213> ORGANISM: Artificial Sequence
<220> FEATURE:
<223> OTHER INFORMATION: Modified human TPO

<400> SEQUENCE: 51

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                 20                  25                  30

His Pro Leu Pro Thr Pro Val Leu Leu Pro Ala Val Asp Phe Ser Leu
             35                  40                  45

Gly Glu Trp Lys Thr Gln Met Glu Glu Thr Lys Ala Gln Asp Ile Leu
 50                  55                  60

Gly Ala Ala Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
```

```
                145                 150                 155                 160
Val Pro Ser Arg Thr Ser Leu Val Leu Thr Leu Asn Glu Leu
            165                 170

<210> SEQ ID NO 52
<211> LENGTH: 174
<212> TYPE: PRT
<213> ORGANISM: Artificial Sequence
<220> FEATURE:
<223> OTHER INFORMATION: Modified human TPO

<400> SEQUENCE: 52

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Thr Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 53
<211> LENGTH: 174
<212> TYPE: PRT
<213> ORGANISM: Artificial Sequence
<220> FEATURE:
<223> OTHER INFORMATION: Modified human TPO

<400> SEQUENCE: 53

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ala Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110
```

```
Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 54
<211> LENGTH: 174
<212> TYPE: PRT
<213> ORGANISM: Artificial Sequence
<220> FEATURE:
<223> OTHER INFORMATION: Modified human TPO

<400> SEQUENCE: 54

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Thr Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 55
<211> LENGTH: 174
<212> TYPE: PRT
<213> ORGANISM: Artificial Sequence
<220> FEATURE:
<223> OTHER INFORMATION: Modified human TPO

<400> SEQUENCE: 55

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Ala Asp Ile Leu
50                  55                  60

Gly Ala Val Thr Leu Leu Leu Glu Gly Val Met Ala Ala Arg Gly Gln
65                  70                  75                  80
```

```
Leu Gly Pro Thr Cys Leu Ser Ser Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 56
<211> LENGTH: 174
<212> TYPE: PRT
<213> ORGANISM: Artificial Sequence
<220> FEATURE:
<223> OTHER INFORMATION: Modified human TPO

<400> SEQUENCE: 56

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Thr Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
            130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 57
<211> LENGTH: 174
<212> TYPE: PRT
<213> ORGANISM: Artificial Sequence
<220> FEATURE:
<223> OTHER INFORMATION: Modified human TPO

<400> SEQUENCE: 57

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
```

```
                35                  40                  45
Gly Glu Trp Lys Thr Gln Ala Glu Thr Lys Ala Gln Asp Ile Leu
 50                  55                  60
Gly Ala Val Thr Leu Leu Leu Glu Gly Val Met Ala Ala Arg Gly Gln
65                  70                  75                  80
Leu Gly Pro Thr Cys Leu Ser Ser Leu Leu Gly Gln Leu Ser Gly Gln
                85                  90                  95
Val Arg Leu Leu Leu Gly Ala Leu Gln Ser Leu Leu Gly Thr Gln Leu
                100                 105                 110
Pro Pro Gln Gly Arg Thr Thr Ala His Lys Asp Pro Asn Ala Ile Phe
                115                 120                 125
Leu Ser Phe Gln His Leu Leu Arg Gly Lys Val Arg Phe Leu Met Leu
            130                 135                 140
Val Gly Gly Ser Thr Leu Cys Val Arg Arg Ala Pro Pro Thr Thr Ala
145                 150                 155                 160
Val Pro Ser Arg Thr Ser Leu Val Leu Thr Leu Asn Glu Leu
                165                 170

<210> SEQ ID NO 58
<211> LENGTH: 174
<212> TYPE: PRT
<213> ORGANISM: Artificial Sequence
<220> FEATURE:
<223> OTHER INFORMATION: Modified human TPO

<400> SEQUENCE: 58

Ser Pro Ala Pro Pro Ala Cys Asp Leu Arg Val Leu Ser Lys Leu Leu
 1               5                  10                  15
Arg Asp Ser His Val Leu His Ser Arg Leu Ser Gln Cys Pro Glu Val
                20                  25                  30
His Pro Leu Pro Thr Pro Val Leu Leu Pro Ala Val Asp Phe Ser Leu
                35                  40                  45
Gly Glu Trp Lys Thr Gln Lys Glu Thr Lys Ala Gln Asp Ile Leu
 50                  55                  60
Gly Ala Val Thr Leu Leu Leu Glu Gly Val Met Ala Ala Arg Gly Gln
65                  70                  75                  80
Leu Gly Pro Thr Cys Leu Ser Ser Leu Leu Gly Gln Leu Ser Gly Gln
                85                  90                  95
Val Arg Leu Leu Leu Gly Ala Leu Gln Ser Leu Leu Gly Thr Gln Leu
                100                 105                 110
Pro Pro Gln Gly Arg Thr Thr Ala His Lys Asp Pro Asn Ala Ile Phe
                115                 120                 125
Leu Ser Phe Gln His Leu Leu Arg Gly Lys Val Arg Phe Leu Met Leu
            130                 135                 140
Val Gly Gly Ser Thr Leu Cys Val Arg Arg Ala Pro Pro Thr Thr Ala
145                 150                 155                 160
Val Pro Ser Arg Thr Ser Leu Val Leu Thr Leu Asn Glu Leu
                165                 170

<210> SEQ ID NO 59
<211> LENGTH: 174
<212> TYPE: PRT
<213> ORGANISM: Artificial Sequence
<220> FEATURE:
<223> OTHER INFORMATION: Modified human TPO

<400> SEQUENCE: 59
```

```
Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Glu Trp Lys Thr Gln Ser Glu Thr Lys Ala Gln Asp Ile Leu
 50                      55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
             100                 105                 110

Pro Pro Gln Gly Arg Thr Thr Ala His Lys Asp Pro Asn Ala Ile Phe
             115                 120                 125

Leu Ser Phe Gln His Leu Leu Arg Gly Lys Val Arg Phe Leu Met Leu
         130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                 165                 170
```

<210> SEQ ID NO 60
<211> LENGTH: 174
<212> TYPE: PRT
<213> ORGANISM: Artificial Sequence
<220> FEATURE:
<223> OTHER INFORMATION: Modified human TPO

<400> SEQUENCE: 60

```
Ser Pro Ala Pro Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Glu Trp Lys Thr Gln Thr Glu Thr Lys Ala Gln Asp Ile Leu
 50                      55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
             100                 105                 110

Pro Pro Gln Gly Arg Thr Thr Ala His Lys Asp Pro Asn Ala Ile Phe
             115                 120                 125

Leu Ser Phe Gln His Leu Leu Arg Gly Lys Val Arg Phe Leu Met Leu
         130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                 165                 170
```

<210> SEQ ID NO 61
<211> LENGTH: 174

```
<212> TYPE: PRT
<213> ORGANISM: Artificial Sequence
<220> FEATURE:
<223> OTHER INFORMATION: Modified human TPO

<400> SEQUENCE: 61

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Ala Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 62
<211> LENGTH: 174
<212> TYPE: PRT
<213> ORGANISM: Artificial Sequence
<220> FEATURE:
<223> OTHER INFORMATION: Modified human TPO

<400> SEQUENCE: 62

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Ser Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160
```

Val Pro Ser Arg Thr Ser Leu Val Leu Thr Leu Asn Glu Leu
            165                 170

<210> SEQ ID NO 63
<211> LENGTH: 174
<212> TYPE: PRT
<213> ORGANISM: Artificial Sequence
<220> FEATURE:
<223> OTHER INFORMATION: Modified human TPO

<400> SEQUENCE: 63

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
            35                  40                  45

Gly Ala Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
            165                 170

<210> SEQ ID NO 64
<211> LENGTH: 174
<212> TYPE: PRT
<213> ORGANISM: Artificial Sequence
<220> FEATURE:
<223> OTHER INFORMATION: Modified human TPO

<400> SEQUENCE: 64

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Ala Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe

-continued

```
                115                 120                 125
Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 65
<211> LENGTH: 174
<212> TYPE: PRT
<213> ORGANISM: Artificial Sequence
<220> FEATURE:
<223> OTHER INFORMATION: Modified human TPO

<400> SEQUENCE: 65

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Ser Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170

<210> SEQ ID NO 66
<211> LENGTH: 174
<212> TYPE: PRT
<213> ORGANISM: Artificial Sequence
<220> FEATURE:
<223> OTHER INFORMATION: Modified human TPO

<400> SEQUENCE: 66

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Thr Leu Leu Glu Gly Val Met Ala Ala Arg Gly Gln
65                  70                  75                  80
```

```
Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170
```

<210> SEQ ID NO 67
<211> LENGTH: 174
<212> TYPE: PRT
<213> ORGANISM: Artificial Sequence
<220> FEATURE:
<223> OTHER INFORMATION: Modified human TPO

<400> SEQUENCE: 67

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Ala Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170
```

<210> SEQ ID NO 68
<211> LENGTH: 174
<212> TYPE: PRT
<213> ORGANISM: Artificial Sequence
<220> FEATURE:
<223> OTHER INFORMATION: Modified human TPO

<400> SEQUENCE: 68

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45
```

```
Gly Glu Trp Lys Thr Gln Met Glu Thr Lys Ala Gln Asp Ile Leu
         50                  55                  60

Gly Ala Val Thr Leu Leu Leu Ala Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170
```

<210> SEQ ID NO 69
<211> LENGTH: 174
<212> TYPE: PRT
<213> ORGANISM: Artificial Sequence
<220> FEATURE:
<223> OTHER INFORMATION: Modified human TPO

<400> SEQUENCE: 69

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
         35                  40                  45

Gly Glu Trp Lys Thr Gln Met Glu Thr Lys Ala Gln Asp Ile Leu
         50                  55                  60

Gly Ala Val Thr Leu Leu Leu Ser Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170
```

<210> SEQ ID NO 70
<211> LENGTH: 174
<212> TYPE: PRT
<213> ORGANISM: Artificial Sequence
<220> FEATURE:
<223> OTHER INFORMATION: Modified human TPO

<400> SEQUENCE: 70

Ser Pro Ala Pro Pro Ala Cys Asp Leu Arg Val Leu Ser Lys Leu Leu

```
                1               5                  10                 15
Arg Asp Ser His Val Leu His Ser Arg Leu Ser Gln Cys Pro Glu Val
                20                 25                 30

His Pro Leu Pro Thr Pro Val Leu Leu Pro Ala Val Asp Phe Ser Leu
                35                 40                 45

Gly Glu Trp Lys Thr Gln Met Glu Glu Thr Lys Arg Gln Asp Ile Leu
                50                 55                 60

Gly Ala Val Thr Leu Leu Leu Glu Gly Val Met Ala Ala Arg Gly Gln
65                 70                 75                 80

Leu Gly Pro Thr Cys Leu Ser Ser Leu Leu Gly Gln Leu Ser Gly Gln
                85                 90                 95

Val Arg Leu Leu Leu Gly Ala Leu Gln Ser Leu Leu Gly Thr Gln Leu
                100                105                110

Pro Pro Gln Gly Arg Thr Thr Ala His Lys Asp Pro Asn Ala Ile Phe
                115                120                125

Leu Ser Phe Gln His Leu Leu Arg Gly Lys Val Arg Phe Leu Met Leu
                130                135                140

Val Gly Gly Ser Thr Leu Cys Val Arg Arg Ala Pro Pro Thr Thr Ala
145                150                155                160

Val Pro Ser Arg Thr Ser Leu Val Leu Thr Leu Asn Glu Leu
                165                170
```

<210> SEQ ID NO 71
<211> LENGTH: 174
<212> TYPE: PRT
<213> ORGANISM: Artificial Sequence
<220> FEATURE:
<223> OTHER INFORMATION: Modified human TPO

<400> SEQUENCE: 71

```
Ser Pro Ala Pro Pro Ala Cys Asp Leu Arg Val Leu Ser Lys Leu Leu
1               5                  10                 15

Arg Asp Ser His Val Leu His Ser Arg Leu Ser Gln Cys Pro Glu Val
                20                 25                 30

His Pro Leu Pro Thr Pro Val Leu Leu Pro Ala Val Asp Phe Ser Leu
                35                 40                 45

Gly Glu Trp Lys Thr Gln Lys Glu Thr Lys Arg Gln Asp Ile Leu
                50                 55                 60

Gly Ala Val Thr Leu Leu Leu Glu Gly Val Met Ala Ala Arg Gly Gln
65                 70                 75                 80

Leu Gly Pro Thr Cys Leu Ser Ser Leu Leu Gly Gln Leu Ser Gly Gln
                85                 90                 95

Val Arg Leu Leu Leu Gly Ala Leu Gln Ser Leu Leu Gly Thr Gln Leu
                100                105                110

Pro Pro Gln Gly Arg Thr Thr Ala His Lys Asp Pro Asn Ala Ile Phe
                115                120                125

Leu Ser Phe Gln His Leu Leu Arg Gly Lys Val Arg Phe Leu Met Leu
                130                135                140

Val Gly Gly Ser Thr Leu Cys Val Arg Arg Ala Pro Pro Thr Thr Ala
145                150                155                160

Val Pro Ser Arg Thr Ser Leu Val Leu Thr Leu Asn Glu Leu
                165                170
```

<210> SEQ ID NO 72
<211> LENGTH: 174
<212> TYPE: PRT

```
<213> ORGANISM: Artificial Sequence
<220> FEATURE:
<223> OTHER INFORMATION: Modified human TPO

<400> SEQUENCE: 72

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Lys Glu Glu Thr Lys Arg Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Ala Pro Ser Arg Thr Ser Leu Val Leu Thr Leu Asn Glu Leu
                165                 170

<210> SEQ ID NO 73
<211> LENGTH: 232
<212> TYPE: PRT
<213> ORGANISM: Artificial Sequence
<220> FEATURE:
<223> OTHER INFORMATION: Modified human Ig G4 Fc domain

<400> SEQUENCE: 73

Glu Pro Lys Ser Ser Asp Lys Thr His Thr Cys Pro Pro Cys Pro Ala
 1               5                  10                  15

Pro Glu Phe Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser Gln Glu Asp Pro Glu Val Gln Phe Asn Trp Tyr Val
50                  55                  60

Asp Gly Val Glu Val His Asn Ala Lys Thr Lys Pro Arg Glu Glu Gln
65                  70                  75                  80

Phe Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
                100                 105                 110

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Gln Glu Glu Met Thr
        130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn His Tyr Thr Gln Lys
    210                 215                 220

Ser Leu Ser Leu Ser Pro Gly Ala
225                 230

<210> SEQ ID NO 74
<211> LENGTH: 15
<212> TYPE: PRT
<213> ORGANISM: homo sapiens

<400> SEQUENCE: 74

Ser Pro Ala Pro Pro Ala Cys Asp Leu Arg Val Leu Ser Lys Leu
1               5                   10                  15

<210> SEQ ID NO 75
<211> LENGTH: 15
<212> TYPE: PRT
<213> ORGANISM: homo sapiens

<400> SEQUENCE: 75

Pro Pro Ala Cys Asp Leu Arg Val Leu Ser Lys Leu Leu Arg Asp
1               5                   10                  15

<210> SEQ ID NO 76
<211> LENGTH: 15
<212> TYPE: PRT
<213> ORGANISM: homo sapiens

<400> SEQUENCE: 76

Cys Asp Leu Arg Val Leu Ser Lys Leu Leu Arg Asp Ser His Val
1               5                   10                  15

<210> SEQ ID NO 77
<211> LENGTH: 15
<212> TYPE: PRT
<213> ORGANISM: homo sapiens

<400> SEQUENCE: 77

Arg Val Leu Ser Lys Leu Leu Arg Asp Ser His Val Leu His Ser
1               5                   10                  15

<210> SEQ ID NO 78
<211> LENGTH: 15
<212> TYPE: PRT
<213> ORGANISM: homo sapiens

<400> SEQUENCE: 78

Ser Lys Leu Leu Arg Asp Ser His Val Leu His Ser Arg Leu Ser
1               5                   10                  15

<210> SEQ ID NO 79
<211> LENGTH: 15
<212> TYPE: PRT
<213> ORGANISM: homo sapiens

<400> SEQUENCE: 79

Leu Arg Asp Ser His Val Leu His Ser Arg Leu Ser Gln Cys Pro
```

```
                1               5                  10                 15
```

<210> SEQ ID NO 80
<211> LENGTH: 15
<212> TYPE: PRT
<213> ORGANISM: homo sapiens

<400> SEQUENCE: 80

```
Ser His Val Leu His Ser Arg Leu Ser Gln Cys Pro Glu Val His
 1               5                  10                  15
```

<210> SEQ ID NO 81
<211> LENGTH: 15
<212> TYPE: PRT
<213> ORGANISM: homo sapiens

<400> SEQUENCE: 81

```
Leu His Ser Arg Leu Ser Gln Cys Pro Glu Val His Pro Leu Pro
 1               5                  10                  15
```

<210> SEQ ID NO 82
<211> LENGTH: 15
<212> TYPE: PRT
<213> ORGANISM: homo sapiens

<400> SEQUENCE: 82

```
Arg Leu Ser Gln Cys Pro Glu Val His Pro Leu Pro Thr Pro Val
 1               5                  10                  15
```

<210> SEQ ID NO 83
<211> LENGTH: 15
<212> TYPE: PRT
<213> ORGANISM: homo sapiens

<400> SEQUENCE: 83

```
Gln Cys Pro Glu Val His Pro Leu Pro Thr Pro Val Leu Leu Pro
 1               5                  10                  15
```

<210> SEQ ID NO 84
<211> LENGTH: 15
<212> TYPE: PRT
<213> ORGANISM: homo sapiens

<400> SEQUENCE: 84

```
Glu Val His Pro Leu Pro Thr Pro Val Leu Leu Pro Ala Val Asp
 1               5                  10                  15
```

<210> SEQ ID NO 85
<211> LENGTH: 15
<212> TYPE: PRT
<213> ORGANISM: homo sapiens

<400> SEQUENCE: 85

```
Pro Leu Pro Thr Pro Val Leu Leu Pro Ala Val Asp Phe Ser Leu
 1               5                  10                  15
```

<210> SEQ ID NO 86
<211> LENGTH: 15
<212> TYPE: PRT
<213> ORGANISM: homo sapiens

<400> SEQUENCE: 86

```
Thr Pro Val Leu Leu Pro Ala Val Asp Phe Ser Leu Gly Glu Trp
 1               5                  10                  15
```

```
<210> SEQ ID NO 87
<211> LENGTH: 15
<212> TYPE: PRT
<213> ORGANISM: homo sapiens

<400> SEQUENCE: 87

Leu Leu Pro Ala Val Asp Phe Ser Leu Gly Glu Trp Lys Thr Gln
 1               5                  10                  15

<210> SEQ ID NO 88
<211> LENGTH: 15
<212> TYPE: PRT
<213> ORGANISM: homo sapiens

<400> SEQUENCE: 88

Ala Val Asp Phe Ser Leu Gly Glu Trp Lys Thr Gln Met Glu Glu
 1               5                  10                  15

<210> SEQ ID NO 89
<211> LENGTH: 15
<212> TYPE: PRT
<213> ORGANISM: homo sapiens

<400> SEQUENCE: 89

Phe Ser Leu Gly Glu Trp Lys Thr Gln Met Glu Glu Thr Lys Ala
 1               5                  10                  15

<210> SEQ ID NO 90
<211> LENGTH: 15
<212> TYPE: PRT
<213> ORGANISM: homo sapiens

<400> SEQUENCE: 90

Gly Glu Trp Lys Thr Gln Met Glu Glu Thr Lys Ala Gln Asp Ile
 1               5                  10                  15

<210> SEQ ID NO 91
<211> LENGTH: 15
<212> TYPE: PRT
<213> ORGANISM: homo sapiens

<400> SEQUENCE: 91

Lys Thr Gln Met Glu Glu Thr Lys Ala Gln Asp Ile Leu Gly Ala
 1               5                  10                  15

<210> SEQ ID NO 92
<211> LENGTH: 15
<212> TYPE: PRT
<213> ORGANISM: homo sapiens

<400> SEQUENCE: 92

Met Glu Glu Thr Lys Ala Gln Asp Ile Leu Gly Ala Val Thr Leu
 1               5                  10                  15

<210> SEQ ID NO 93
<211> LENGTH: 15
<212> TYPE: PRT
<213> ORGANISM: homo sapiens

<400> SEQUENCE: 93

Thr Lys Ala Gln Asp Ile Leu Gly Ala Val Thr Leu Leu Leu Glu
 1               5                  10                  15

<210> SEQ ID NO 94
```

```
<211> LENGTH: 15
<212> TYPE: PRT
<213> ORGANISM: homo sapiens

<400> SEQUENCE: 94

Gln Asp Ile Leu Gly Ala Val Thr Leu Leu Glu Gly Val Met
1               5                   10                  15

<210> SEQ ID NO 95
<211> LENGTH: 15
<212> TYPE: PRT
<213> ORGANISM: homo sapiens

<400> SEQUENCE: 95

Leu Gly Ala Val Thr Leu Leu Leu Glu Gly Val Met Ala Ala Arg
1               5                   10                  15

<210> SEQ ID NO 96
<211> LENGTH: 15
<212> TYPE: PRT
<213> ORGANISM: homo sapiens

<400> SEQUENCE: 96

Val Thr Leu Leu Leu Glu Gly Val Met Ala Ala Arg Gly Gln Leu
1               5                   10                  15

<210> SEQ ID NO 97
<211> LENGTH: 15
<212> TYPE: PRT
<213> ORGANISM: homo sapiens

<400> SEQUENCE: 97

Leu Leu Glu Gly Val Met Ala Ala Arg Gly Gln Leu Gly Pro Thr
1               5                   10                  15

<210> SEQ ID NO 98
<211> LENGTH: 15
<212> TYPE: PRT
<213> ORGANISM: homo sapiens

<400> SEQUENCE: 98

Gly Val Met Ala Ala Arg Gly Gln Leu Gly Pro Thr Cys Leu Ser
1               5                   10                  15

<210> SEQ ID NO 99
<211> LENGTH: 15
<212> TYPE: PRT
<213> ORGANISM: homo sapiens

<400> SEQUENCE: 99

Ala Ala Arg Gly Gln Leu Gly Pro Thr Cys Leu Ser Ser Leu Leu
1               5                   10                  15

<210> SEQ ID NO 100
<211> LENGTH: 15
<212> TYPE: PRT
<213> ORGANISM: homo sapiens

<400> SEQUENCE: 100

Gly Gln Leu Gly Pro Thr Cys Leu Ser Ser Leu Leu Gly Gln Leu
1               5                   10                  15

<210> SEQ ID NO 101
<211> LENGTH: 15
<212> TYPE: PRT
```

<213> ORGANISM: homo sapiens

<400> SEQUENCE: 101

Gly Pro Thr Cys Leu Ser Ser Leu Leu Gly Gln Leu Ser Gly Gln
1               5                   10                  15

<210> SEQ ID NO 102
<211> LENGTH: 15
<212> TYPE: PRT
<213> ORGANISM: homo sapiens

<400> SEQUENCE: 102

Cys Leu Ser Ser Leu Leu Gly Gln Leu Ser Gly Gln Val Arg Leu
1               5                   10                  15

<210> SEQ ID NO 103
<211> LENGTH: 15
<212> TYPE: PRT
<213> ORGANISM: homo sapiens

<400> SEQUENCE: 103

Ser Leu Leu Gly Gln Leu Ser Gly Gln Val Arg Leu Leu Leu Gly
1               5                   10                  15

<210> SEQ ID NO 104
<211> LENGTH: 15
<212> TYPE: PRT
<213> ORGANISM: homo sapiens

<400> SEQUENCE: 104

Gly Gln Leu Ser Gly Gln Val Arg Leu Leu Leu Gly Ala Leu Gln
1               5                   10                  15

<210> SEQ ID NO 105
<211> LENGTH: 15
<212> TYPE: PRT
<213> ORGANISM: homo sapiens

<400> SEQUENCE: 105

Ser Gly Gln Val Arg Leu Leu Leu Gly Ala Leu Gln Ser Leu Leu
1               5                   10                  15

<210> SEQ ID NO 106
<211> LENGTH: 15
<212> TYPE: PRT
<213> ORGANISM: homo sapiens

<400> SEQUENCE: 106

Val Arg Leu Leu Leu Gly Ala Leu Gln Ser Leu Leu Gly Thr Gln
1               5                   10                  15

<210> SEQ ID NO 107
<211> LENGTH: 15
<212> TYPE: PRT
<213> ORGANISM: homo sapiens

<400> SEQUENCE: 107

Leu Leu Gly Ala Leu Gln Ser Leu Leu Gly Thr Gln Leu Pro Pro
1               5                   10                  15

<210> SEQ ID NO 108
<211> LENGTH: 15
<212> TYPE: PRT
<213> ORGANISM: homo sapiens

```
<400> SEQUENCE: 108

Ala Leu Gln Ser Leu Leu Gly Thr Gln Leu Pro Pro Gln Gly Arg
 1               5                  10                  15

<210> SEQ ID NO 109
<211> LENGTH: 15
<212> TYPE: PRT
<213> ORGANISM: homo sapiens

<400> SEQUENCE: 109

Ser Leu Leu Gly Thr Gln Leu Pro Pro Gln Gly Arg Thr Thr Ala
 1               5                  10                  15

<210> SEQ ID NO 110
<211> LENGTH: 15
<212> TYPE: PRT
<213> ORGANISM: homo sapiens

<400> SEQUENCE: 110

Gly Thr Gln Leu Pro Pro Gln Gly Arg Thr Thr Ala His Lys Asp
 1               5                  10                  15

<210> SEQ ID NO 111
<211> LENGTH: 15
<212> TYPE: PRT
<213> ORGANISM: homo sapiens

<400> SEQUENCE: 111

Leu Pro Pro Gln Gly Arg Thr Thr Ala His Lys Asp Pro Asn Ala
 1               5                  10                  15

<210> SEQ ID NO 112
<211> LENGTH: 15
<212> TYPE: PRT
<213> ORGANISM: homo sapiens

<400> SEQUENCE: 112

Gln Gly Arg Thr Thr Ala His Lys Asp Pro Asn Ala Ile Phe Leu
 1               5                  10                  15

<210> SEQ ID NO 113
<211> LENGTH: 15
<212> TYPE: PRT
<213> ORGANISM: homo sapiens

<400> SEQUENCE: 113

Thr Thr Ala His Lys Asp Pro Asn Ala Ile Phe Leu Ser Phe Gln
 1               5                  10                  15

<210> SEQ ID NO 114
<211> LENGTH: 15
<212> TYPE: PRT
<213> ORGANISM: homo sapiens

<400> SEQUENCE: 114

His Lys Asp Pro Asn Ala Ile Phe Leu Ser Phe Gln His Leu Leu
 1               5                  10                  15

<210> SEQ ID NO 115
<211> LENGTH: 15
<212> TYPE: PRT
<213> ORGANISM: homo sapiens

<400> SEQUENCE: 115
```

-continued

Pro Asn Ala Ile Phe Leu Ser Phe Gln His Leu Leu Arg Gly Lys
1               5                   10                  15

<210> SEQ ID NO 116
<211> LENGTH: 15
<212> TYPE: PRT
<213> ORGANISM: homo sapiens

<400> SEQUENCE: 116

Ile Phe Leu Ser Phe Gln His Leu Leu Arg Gly Lys Val Arg Phe
1               5                   10                  15

<210> SEQ ID NO 117
<211> LENGTH: 15
<212> TYPE: PRT
<213> ORGANISM: homo sapiens

<400> SEQUENCE: 117

Ser Phe Gln His Leu Leu Arg Gly Lys Val Arg Phe Leu Met Leu
1               5                   10                  15

<210> SEQ ID NO 118
<211> LENGTH: 15
<212> TYPE: PRT
<213> ORGANISM: homo sapiens

<400> SEQUENCE: 118

His Leu Leu Arg Gly Lys Val Arg Phe Leu Met Leu Val Gly Gly
1               5                   10                  15

<210> SEQ ID NO 119
<211> LENGTH: 15
<212> TYPE: PRT
<213> ORGANISM: homo sapiens

<400> SEQUENCE: 119

Arg Gly Lys Val Arg Phe Leu Met Leu Val Gly Gly Ser Thr Leu
1               5                   10                  15

<210> SEQ ID NO 120
<211> LENGTH: 15
<212> TYPE: PRT
<213> ORGANISM: homo sapiens

<400> SEQUENCE: 120

Val Arg Phe Leu Met Leu Val Gly Gly Ser Thr Leu Cys Val Arg
1               5                   10                  15

<210> SEQ ID NO 121
<211> LENGTH: 15
<212> TYPE: PRT
<213> ORGANISM: homo sapiens

<400> SEQUENCE: 121

Leu Met Leu Val Gly Gly Ser Thr Leu Cys Val Arg Arg Ala Pro
1               5                   10                  15

<210> SEQ ID NO 122
<211> LENGTH: 15
<212> TYPE: PRT
<213> ORGANISM: homo sapiens

<400> SEQUENCE: 122

Val Gly Gly Ser Thr Leu Cys Val Arg Arg Ala Pro Pro Thr Thr
1               5                   10                  15

<210> SEQ ID NO 123
<211> LENGTH: 15
<212> TYPE: PRT
<213> ORGANISM: homo sapiens

<400> SEQUENCE: 123

Ser Thr Leu Cys Val Arg Arg Ala Pro Pro Thr Thr Ala Val Pro
1               5                   10                  15

<210> SEQ ID NO 124
<211> LENGTH: 15
<212> TYPE: PRT
<213> ORGANISM: homo sapiens

<400> SEQUENCE: 124

Cys Val Arg Arg Ala Pro Pro Thr Thr Ala Val Pro Ser Arg Thr
1               5                   10                  15

<210> SEQ ID NO 125
<211> LENGTH: 15
<212> TYPE: PRT
<213> ORGANISM: homo sapiens

<400> SEQUENCE: 125

Arg Ala Pro Pro Thr Thr Ala Val Pro Ser Arg Thr Ser Leu Val
1               5                   10                  15

<210> SEQ ID NO 126
<211> LENGTH: 15
<212> TYPE: PRT
<213> ORGANISM: homo sapiens

<400> SEQUENCE: 126

Pro Thr Thr Ala Val Pro Ser Arg Thr Ser Leu Val Leu Thr Leu
1               5                   10                  15

<210> SEQ ID NO 127
<211> LENGTH: 15
<212> TYPE: PRT
<213> ORGANISM: homo sapiens

<400> SEQUENCE: 127

Ala Val Pro Ser Arg Thr Ser Leu Val Leu Thr Leu Asn Glu Leu
1               5                   10                  15

<210> SEQ ID NO 128
<211> LENGTH: 15
<212> TYPE: PRT
<213> ORGANISM: homo sapiens

<400> SEQUENCE: 128

Ser Arg Thr Ser Leu Val Leu Thr Leu Asn Glu Leu Pro Asn Arg
1               5                   10                  15

<210> SEQ ID NO 129
<211> LENGTH: 27
<212> TYPE: PRT
<213> ORGANISM: Artificial Sequence
<220> FEATURE:
<223> OTHER INFORMATION: Modified human TPO

<400> SEQUENCE: 129

Gly Glu Trp Lys Thr Gln Lys Glu Glu Thr Lys Ala Gln Asp Ile Leu
1               5                   10                  15

Gly Ala Val Thr Leu Leu Leu Glu Gly Val Met
            20                  25

<210> SEQ ID NO 130
<211> LENGTH: 27
<212> TYPE: PRT
<213> ORGANISM: Artificial Sequence
<220> FEATURE:
<223> OTHER INFORMATION: Modified human TPO

<400> SEQUENCE: 130

Gly Glu Trp Lys Thr Gln Met Glu Glu Arg Lys Ala Gln Asp Ile Leu
1               5                   10                  15

Gly Ala Val Thr Leu Leu Leu Glu Gly Val Met
            20                  25

<210> SEQ ID NO 131
<211> LENGTH: 27
<212> TYPE: PRT
<213> ORGANISM: Artificial Sequence
<220> FEATURE:
<223> OTHER INFORMATION: Modified human TPO

<400> SEQUENCE: 131

Gly Glu Trp Lys Thr Gln Met Glu Glu Thr Lys Arg Gln Asp Ile Leu
1               5                   10                  15

Gly Ala Val Thr Leu Leu Leu Glu Gly Val Met
            20                  25

<210> SEQ ID NO 132
<211> LENGTH: 27
<212> TYPE: PRT
<213> ORGANISM: Artificial Sequence
<220> FEATURE:
<223> OTHER INFORMATION: Modified human TPO

<400> SEQUENCE: 132

Gly Glu Trp Lys Thr Gln Met Glu Glu Thr Lys Ala Gln Arg Ile Leu
1               5                   10                  15

Gly Ala Val Thr Leu Leu Leu Glu Gly Val Met
            20                  25

<210> SEQ ID NO 133
<211> LENGTH: 27
<212> TYPE: PRT
<213> ORGANISM: Artificial Sequence
<220> FEATURE:
<223> OTHER INFORMATION: Modified human TPO

<400> SEQUENCE: 133

Gly Glu Trp Lys Thr Gln Met Glu Glu Thr Lys Ala Gln Asp Ile Leu
1               5                   10                  15

Gly Ala Val Thr Ala Leu Leu Glu Gly Val Met
            20                  25

<210> SEQ ID NO 134
<211> LENGTH: 27
<212> TYPE: PRT
<213> ORGANISM: Artificial Sequence
<220> FEATURE:
<223> OTHER INFORMATION: Modified human TPO

<400> SEQUENCE: 134

Gly Glu Trp Lys Thr Gln Met Glu Glu Thr Lys Ala Gln Asp Ile Leu

```
                1               5                  10              15

Gly Ala Val Thr Leu Ala Leu Glu Gly Val Met
                20                 25

<210> SEQ ID NO 135
<211> LENGTH: 15
<212> TYPE: PRT
<213> ORGANISM: Artificial Sequence
<220> FEATURE:
<223> OTHER INFORMATION: Modified human TPO

<400> SEQUENCE: 135

Pro Thr Thr Ala Ala Pro Ser Arg Thr Ser Leu Val Leu Thr Leu
  1               5                  10              15

<210> SEQ ID NO 136
<211> LENGTH: 15
<212> TYPE: PRT
<213> ORGANISM: Artificial Sequence
<220> FEATURE:
<223> OTHER INFORMATION: Modified human TPO

<400> SEQUENCE: 136

Pro Thr Thr Ala Asn Pro Ser Arg Thr Ser Leu Val Leu Thr Leu
  1               5                  10              15

<210> SEQ ID NO 137
<211> LENGTH: 15
<212> TYPE: PRT
<213> ORGANISM: Artificial Sequence
<220> FEATURE:
<223> OTHER INFORMATION: Modified human TPO

<400> SEQUENCE: 137

Pro Thr Thr Ala Arg Pro Ser Arg Thr Ser Leu Val Leu Thr Leu
  1               5                  10              15

<210> SEQ ID NO 138
<211> LENGTH: 15
<212> TYPE: PRT
<213> ORGANISM: Artificial Sequence
<220> FEATURE:
<223> OTHER INFORMATION: Modified human TPO

<400> SEQUENCE: 138

Pro Thr Thr Ala Thr Pro Ser Arg Thr Ser Leu Val Leu Thr Leu
  1               5                  10              15
```

THROMBOPOIETIN PROTEINS WITH IMPROVED PROPERTIES

This application is the National Stage of International Application No. PCT/EP2004/006887, filed on Jun. 25, 2004.

FIELD

The invention concerns human thrombopoietin and in particular modified forms of thrombopoietin (TPO) with improved properties. The improved proteins contain amino acid substitutions at specific positions within the TPO molecule. The invention provides modified TPO molecules, preferably fusion proteins comprising immunoglobulin constant regions and modified human TPO, with improved biological activity concomitant with reduced immunogenic potential in the protein. The improved proteins are intended for therapeutic use in the treatment of diseases in humans.

BACKGROUND

Thrombopoietin (TPO) is a glycoprotein hormone involved regulation of platelet production. TPO promotes both the proliferation of megakaryocyte progenitors in the bone marrow and their maturation into platelet-producing megakaryocytes.

TPO has significant therapeutic value in the treatment of patients with reduced platelet count. In particular patients with many types of cancer suffer thrombocytopenias on account of myelosuppressive chemotherapy. Platelet transfusion has historically been the mainstay by which such patients have been supported. The availability of purified TPO from recombinant sources could enhance the options available for aggressive chemotherapy regimens and other patients at risk of bleeding complications due to their thrombocytopenia [Prow, D. & Vadhan-Raj, S. (1998) *Oncology* 12: 1597-1608].

At least two forms of recombinant human TPO have been developed for clinical trails. A truncated version comprising only the N-terminal 163 amino acids conjugated with polyethylene glycol is referred to as pegylated recombinant human megakaryocyte growth and development factor (PEG-rHuMDGF). A full length and glycosylated molecule is referred to as recombinant human thrombopoietin (rhTPO).

Both forms of TPO have been evaluated in Phase I/II trials, where they were given to cancer patients before receiving chemotherapy in order to boost platelet counts. The results of these trials have been reported [Basser R. L. et al (1996) Lancet; 348: 1279-1281; Basser R. L. et al (1997) Blood; 89: 3118-3128. Erratum in 1997; 90: 2513; Fannuchi M. et al, (1997), New England Journal of Medicine; 336: 404-409; Vadhan-Raj S. et al. (1997) Ann. Intern. Med; 126: 673-681 and Vadhan-Raj S. (1998) Semin. Hematol; 35: 261-268].

Both forms of TPO have been found to be immunogenic in a small proportion of subjects, and neutralising antibodies have also been demonstrated to both molecules [Hardy L, et al (1997) The Toxicologist; 36: 277; Li J, et al (2001) Blood; 98: 3241-3248; Koren E. (2002) Dev Biol (Basel); 109: 87-95; Basser R. L. et al (2002), Blood; 99: 2599-2602 and Koren E. (2002) Current Pharmaceutical Biotechnology; 3:349-360].

Clinical trials of PEG-rHuMDGF were abandoned in 1998 as neutralising antibodies could bind to endogenous TPO causing some of the patients and normal volunteers involved in the trials to become platelet transfusion dependent for several years. [Neumann T. A & Foote M. (2000) Cytokines Cell Mol Ther.: 6; 47-56].

Clearly for these subjects, an immune response has been mounted to the therapeutic TPO despite the fact that TPO is normally present in the circulation. The pivotal feature leading to the induction of an immune response is the presence within the protein of peptides that can stimulate the activity of T-cells via presentation on MHC class II molecules. Such peptide sequences are "T-cell epitopes" and are commonly defined as any amino acid residue sequence with the ability to bind to MHC Class II molecules. Implicitly, a "T-cell epitope" means an epitope which when bound to MHC molecules can be recognised by a T-cell receptor (TCR), and which can, at least in principle, cause the activation of these T-cells by engaging a TCR to promote a T-cell response. Patients who develop antibodies to TPO possess T cells that are capable of recognising peptide fragments of TPO bound to MHC class II molecules in their T cell repertoire.

To date no form of TPO has received regulatory approval as a therapeutic compound. From the foregoing there is clearly a continued need for TPO analogues with enhanced properties. There is a particular need for enhancement of the in vivo characteristics when administered to the human subject. In this regard, it is highly desired to provide TPO with reduced or absent potential to induce an immune response and enhanced biological potency in the human subject.

Others have provided TPO molecules and analogues [U.S. Pat. Nos. 5,989,538; U.S. Pat. No. 6,083,913; 5,879,673] including chemically modified and truncated forms [U.S. Pat. No. 5,989,538] and TPO fusion proteins [U.S. Pat. No. 6,066,318].

Koren et al [US Patent Application 20030077756] have identified peptide sequences in the C-terminal domain of human TPO that are able to interact with anti-TPO antibodies.

None of these teachings recognise the importance of T cell epitopes to the immunogenic properties of the protein nor have been conceived to directly influence said properties in a specific and controlled way according to the scheme of the present invention.

WO 03/104263 describes methods for the identification of CD4+ T-cell epitopes in cytokines including TPO. According to this method an epitope at residues 154-171 was defined. However, substitutions leading to a desired altered immunogenic response were suggested at residues outside of the epitope at residues 138, 139 and 140.

The co-owned application WO 02/068469 describes the results of an analysis of the entire TPO sequence for the presence of potential MHC class II binding ligands. The analysis therein is conducted using a computer simulation of the peptide MHC binding interaction. WO 02/068469 also provides multiple amino acid substitutions for achieving the disruption of the said potential epitope sequences.

The present invention is concerned also with TPO molecules in which amino acid substitution and or combinations of substitution have been conducted. In the present case, the molecules of the invention are fusion proteins comprising a human immunoglobulin constant region moiety linked with a human TPO mutein. Linkage to the immunoglobulin constant region domain causes the protein to become dimeric and these molecules additionally show increased potency.

This structure together with substitutions and combinations of substitutions in the TPO component confer the property of enhancing the biological activity of the molecule and also achieve a reduced immunogenic profile for the protein.

The general category of "human Fc fusion proteins" of which the present molecules are examples have been described previously [U.S. Pat. Nos. 5,541,087; 5,726,044 Lo et al (1998), *Protein Engineering* 11:495-500].

SUMMARY OF THE INVENTION

The invention provides human thrombopoietin molecules containing amino acid substitutions. The amino acid substitutions confer improved properties to the protein. The improved properties concern the specific biological activity of the protein and also the immunogenic properties of the protein.

The molecules of the invention are fusion proteins comprising a human immunoglobulin heavy chain constant region moiety linked with a human TPO mutein derived from wild-type truncated TPO (1-174).

The TPO proteins of the invention preferably are expressed in mammalian cell-lines as a C-terminal fusion partner, linked to the Fc unit of human IgG$_4$, wherein the Fc portion may include a hinge region.

The TPO sequence is fused preferably to the C-terminus of a hinge modified/C$_H$2/C$_H$3 Fc region of human IgG$_4$ via a 15 amino acid flexible linker between the C-terminus of the C$_H$3 and the N-terminus of TPO$_{(1-174)}$. The expressed fusion proteins are dimeric and have a stoichiometry of (hinge-C$_H$2—C$_H$3-linker-TPO$_{(1-174)}$)$_2$.

The molecules of the invention have new properties. Such molecules may cause benefit for a patient with thrombocytopenia.

The molecules of the invention are characterised by the protein sequences defined herein as M1 to M67, F-M1 to F-M67, and F-L-M1 to F-L-M67, respectively, wherein M1 to M67 represent the protein sequences of differently modified human TPO in its truncated form (1-174), F-M1 to F-M67 represent the respective fusion proteins with the Fc portion of human IgG4 or optionally another human IgG form, and F-L-M1 to F-L-M67 represent the respective fusion proteins comprising a linker molecule between the Fc sequence and the TPO protein sequence, wherein said linker molecule is preferably a linker peptide comprising 4-20 amino acid residues.

The molecules of the invention are further characterised their relative activity in a proliferation assay of between 0.1 and 6.3.

A most preferred molecule of the invention is characterised by the protein sequence M67 or F-M67 or F-L-M67 or F1-L1-M67, wherein F is a Fc portion, preferably deriving from human IgG4 and including a modified hinge, and L is a peptide linker of 15 amino acid residues and F1 and L1 are specific sequences according to Table A3 and A4. These molecules are further characterised by a relative activity of around 0.4 in a proliferation assay.

A further preferred molecule of the invention is characterised by the protein sequences M1, F-M1, F-L-M1, and preferably F1-L1-M1 and is further characterised by a relative activity of around 1.0 in a proliferation assay.

A further preferred molecule of the invention is characterised by the protein sequences M66, F-M66, F-L-M66, and preferably F1-L1-M66 and is further characterised by a relative activity of around 0.2 in a proliferation assay.

The most preferred molecules of the invention are characterised yet further still by comprising sequences demonstrated to show reduced immunogenicity in human cells. In particular reduced immunogenicity as measured using a "T-cell assay" or a "time course assay" as defined herein.

The present invention provides for modified forms of TPO proteins, preferably immunoglobulin fusion proteins having the biological activity of human TPO, that are expected to display enhanced properties in vivo. The present invention discloses the major regions of the TPO primary sequence that are immunogenic in man and provides modification to the sequences to eliminate or reduce the immunogenic effectiveness of these sites.

In one embodiment, synthetic peptides comprising the immunogenic regions can be provided in pharmaceutical composition for the purpose of promoting a tolerogenic response to the whole molecule.

In a further embodiment, the modified TPO molecules of the present invention can be used in pharmaceutical compositions.

In summary the invention is concerned with the following issues:

A modified TPO molecule (M) in a truncated (1-174) form having essentially the same biological specificity and activity of human TPO when used in vivo containing one or more amino acid substitutions, wherein said modified TPO molecule is substantially non-immunogenic or less immunogenic than the parental non-modified human TPO and said amino acid substitutions cause a reduction or an elimination of one or more of T-cell epitopes within the wild-type TPO sequence which act in the parental non-modified molecule as MHC class II binding ligands and stimulate T-cells.

A modified TPO molecule as specified containing one or more of the amino acid substitutions containing at least the amino acid substitutions M55K, A60R and V161A within the TPO sequence.

A modified human TPO molecule having the formula/structure (M)

```
SPAPPACDLRVLSKLLRDSHVLHSRLSQCPEVHPLPTPVLLPAVDFSLG
X¹X²KTQX³EEX⁴KX⁵X⁶DX⁷LGAX⁸TX⁹LX¹⁰X¹¹TVMAARGQLGPTCL
SSLLGQLSGQVRLLLGALQSLLGTQLPPQGRTTAHKDPNAIFLSFQHLLR
GKVRFLMLVGGSTLCVRRAPPTTAX¹²X¹³SRTSLVLTLNEL
(SEQ ID NO: 1),
``` wherein
  $X^1$ is A, E;
  $X^2$ is S, W;
  $X^3$ is A or T or K, S or M;
  $X^4$ is A, T;
  $X^5$ is R, A;
  $X^6$ is A or T or Q;
  $X^7$ is A or T or I;
  $X^8$ is A or T or V;
  $X^9$ is A or T or S or L;
  $X^{10}$ is A or L;
  $X^{11}$ is A or S or E;
  $X^{12}$ is N or A or T or R or E or D or G or H or P or K or Q or V;
  $X^{13}$ is A or P,
  and whereby simultaneously $X^1$=E, $X^2$=W, $X^3$=M, $X^4$=T, $X^5$=A, $X^6$=Q, $X^7$=I, $X^8$=V, $X^9$=L, $X^{10}$=L, $X^{11}$=E, $X^{12}$=V and $X^{13}$=P are excluded, said meanings representing the native human TPO.

A modified TPO molecule (M) as specified having a protein sequence selected from the group consisting of M1 to M67, wherein M1-M67 are specified in Table A1.

A modified TPO molecule (M) as specified having a protein sequence of M1, M67 or M68 as specified in Table A1.

A fusion protein of the structure

F-(L)n-M comprising a modified human TPO molecule (M) as specified, fused directly (n=0) or indirectly (n=1) via a linker molecule (L) to a human immunoglobulin heavy constant region domain (F).

A fusion protein as specified, wherein F is an Fc domain, optionally comprising a hinge region, wherein this hinge region may be modified.

A fusion protein as specified wherein the C-terminus of the human immunoglobulin heavy constant region domain (Fc domain) is linked directly or indirectly to the N-terminus of the modified TPO.

A dimeric fusion protein comprising two monomeric fusion protein chains as specified.

A fusion protein as specified, wherein said TPO portion contains one or more of the amino acid substitutions M55K, A60R and V161A within the TPO domain.

A fusion protein as specified, wherein said TPO portion has the formula/structure (M):

```
SPAPPACDLRVLSKLLRDSHVLHSRLSQCPEVHPLPTPVLLPAVDFSLG
X¹X²KTQX³EEX⁴KX⁵X⁶DX⁷LGAX⁸TX⁹LX¹⁰X¹¹GVMAARGQLGPTCL
SSLLGQLSGQVRLLLGALQSLLGTQLPPQGRTTAHKDPNAIFLSFQHLLR
GKVRFLMLVGGSTLCVRRAPPTTAX¹²X¹³SRTSLVLTLNEL
(SEQ ID NO: 1),
``` wherein
$X^1$ is A, E;
$X^2$ is S, W;
$X^3$ is A or T or K, S or M;
$X^4$ is A, T;
$X^5$ is R, A;
$X^6$ is A or T or Q;
$X^7$ is A or T or I;
$X^8$ is A or T or V;
$X^9$ is A or T or S or L;
$X^{10}$ is A or L;
$X^{11}$ is A or S or E;
$X^{12}$ is N or A or T or R or E or D or G or H or P or K or Q or V;
$X^{13}$ is A or P,
and whereby simultaneously $X^1$=E, $X^2$=W, $X^3$=M, $X^4$=T, $X^5$=A, $X^6$=Q, $X^7$=I, $X^8$=V, $X^9$=L, $X^{10}$=L, $X^{11}$=E, $X^{12}$=V and $X^{13}$=P are excluded.

A fusion protein as specified in Table A5 or A6, wherein said TPO portion has a protein sequence selected from the group M1 to M67, wherein M1-M67 are specified in Table A1.

A fusion protein as specified in Table A5 or A6, wherein F has the sequence F1 as specified in Table A3.

A fusion protein as specified in Table A5 or A6, wherein L has the sequence L1 as specified in Table A4.

A fusion protein as specified selected from the group consisting of a member of Table A7.

A fusion protein selected from the group comsisting of
F-M1, F-L-M1, F1-L1-M1;
F-M66, F-L-M66, F1-L1-M66, and
F-M67, F-L-M67, F1-L1-M67,
wherein F is an immunoglobulin heavy chain constant region, F1 is the immunoglobulin heavy chain constant region of Table A3, L is a linker molecule, and L1 is the linker peptide of Table A4.

A peptide molecule selected from the group consisting of
GEWKTQMEETKAQDILGAVTLLLEGVM (SEQ ID NO: 2);
PTTAVPSRTSLVLTL (SEQ ID NO: 3);
or a sequence track consisting of at least 9 consecutive amino acid residues of any of said peptide molecules having a potential MHC class II binding activity and created from the primary sequence of non-modified human TPO in its truncated form (1-174), whereby said peptide molecule or sequence track has a stimulation index of >1.8 in a biological assay of cellular proliferation and said index is taken as the value of cellular proliferation scored following stimulation by a peptide and divided by the value of cellular proliferation scored in control cells not in receipt peptide and wherein cellular proliferation is measured by any suitable means.

Use of said peptide molecule for the manufacture of a vaccine in order to reduce immunogenicity to TPO in a patient A modified peptide molecule deriving from any peptide molecule as specified having a reduced or absent potential MHC class II binding activity expressed by a stimulation index of less than 2, whereby said index is taken as the value of cellular proliferation scored following stimulation by a peptide and divided by the value of cellular proliferation scored in control cells not in receipt peptide and wherein cellular proliferation is measured by any suitable means.

Use of said modified peptide molecule for the manufacture of a modified TPO molecule or a fusion protein comprising an Fc portion of an immunoglobulin and said modified TPO.

A modified TPO molecule having the biological activity of human thrombopoietin and comprising a human Fc domain and containing at least the amino acid substitutions A60R and V161A within the thrombopoietin domain and being further characterised by exhibiting a relative activity of around 1.0;

A modified TPO molecule having the biological activity of human thrombopoietin and comprising a human Fc domain and containing at least the amino acid substitutions M55K, A60R and V161A within the thrombopoietin domain and being further characterised by exhibiting a relative activity of around 0.4;

The mutant proteins of the present invention are readily made using recombinant DNA techniques well known in the art and the invention provides methods for the recombinant production of such molecules.

In as far as this invention relates to modified TPO, compositions containing such modified TPO proteins or fragments of modified TPO proteins and related compositions should be considered within the scope of the invention. In another aspect, the present invention relates to nucleic acids encoding modified TPO entities. In a further aspect the present invention relates to methods for therapeutic treatment of humans using the modified TPO proteins.

DETAILED DESCRIPTION OF THE INVENTION

In nature, the mature TPO protein is single polypeptide of 332 amino acids The amino acid sequence of TPO (depicted as single-letter code) is as follows (M68):

```
SPAPPACDLRVLSKLLRDSHVLHSRLSQCPEVHPLPTPVLLPAVDFSLGE
WKTQMEETKAQDILGAVTLLLEGVMAARGQLGPTCLSSLLGQLSGQVRLL
LGALQSLLGTQLPPQGRTTAHKDPNAIFLSFQHLLRGKVRFLMLVGGSTL
CVRRAPPTTAVPSRTSLVLTLNELPNRTSGLLETNFTASARTTGSGLLKW
QQGFRAKIPGLLNQTSRSLDQIPGYLNRIHELLNGTRGLFPGPSRRTLGA
PDISSGTSDTGSLPPNLQPGYSPSPTHPPTGQYTLFPLPPTLPTPVVQLH
PLLDPSAPTPTPTSPLLNTSYTHSQNLSQEG (SEQ ID NO: 4).
```

The mature protein comprises distinct regions with the N-terminal domain highly conserved between mouse and man and significant homology with erythropoietin and interferon-alpha and interferon-beta [de Sauvage, F. J. et al (1994) *Nature* 369: 533-538; Chang, M. et al (1995) *J. Biol. Chem.* 270: 511-514. The C-terminal domain has several sites for N-linked glycosylation. The N-terminal domain is sufficient for the thrombopoietic effect of the molecule whereas the C-terminal region is likely important in maintaining the circulating half-life in vivo [Foster, D. et al (1996) *Stem Cells* 14: 102-107].

The term "TPO" is used herein to denote human thrombopoietin. In some instances the term is also used more broadly herein to include fusion proteins (see below) comprising a TPO moiety and or more especially a TPO mutein.

The term "mutein" is used herein to denote a TPO protein engineered to contain one or more amino acid substitutions differing from the above native sequence.

In addition, the TPO muteins of the invention each represent a truncated version of the native sequence and comprise residues only residues 1-174 of the above sequence thereby encompassing the complete N-terminal domain of the native protein.

"TPO muteins" and "TPO fusion proteins" according to the invention refer to proteins comprising a TPO domain of 174 residues.

Other TPO muteins and TPO fusion proteins comprising more or less than 174 residues of TPO sequence may be contemplated and fall under the scope of the present. Thus TPO fusion proteins comprising residues 1-164 or 1-165 or 1-166 or 1-167 or 1-168 or 1-169 or 1-170 or 1-171 or 1-172 or 1-173 can be contemplated and may be expected to have properties equivalent to the preferred molecules of the invention.

The term "peptide" as used herein, is a compound that includes two or more amino acids. The amino acids are linked together by a peptide bond.

A peptide bond is the sole covalent linkage between amino acids in the linear backbone structure of all peptides, polypeptides or proteins. The peptide bond is a covalent bond, planar in structure and chemically constitutes a substituted amide. An "amide" is any of a group of organic compounds containing the grouping —CONH—.

There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins—that can be formed is practically unlimited.

Since the peptide bond is the sole linkage between amino acids, all peptides, polypeptides or proteins have defined termini conventionally referred to as the "N-terminus" or "N-terminal" residue and the "C-terminus" or "C-terminal residue". The N-terminal residue bears a free amino group, whereas the C-terminal residue bears a free carboxyl group.

All sequences of consecutive amino acids accordingly have an orientation N-terminal to C-terminal. Where fusion proteins are constituted or differing domains are connected within a protein species their relative orientation may be described as "N-terminal" or "C-terminal".

The term "fusion protein" is used herein to refer to a protein molecule comprising two or more functionally distinct protein domains within a single polypeptide chain. The protein moieties in the fusion protein may be directly coupled or may be joined via a linker peptide.

A "linker" or "linker peptide" refers herein to a peptide segment joining two moieties of fusion protein. An example of a linker peptide is provided by the amino acid sequence $(G)_4S(G)_4S(G)_3SG$ (SEQ ID NO: 5). However, also other linker peptides, preferably having 4-20 amino acid residues can be used according to the invention. The fusion proteins of the present invention contain such a linker but not all fusion proteins contain a linker.

Fusion proteins are commonly produced by means of recombinant DNA techniques and as such can be considered artificial proteins having no direct counterparts in nature (natural fusion proteins can arise, for example via chromosomal translocation, but are not considered here). An example of a fusion protein is a fusion in which an immunoglobulin Fc region is placed at the N-terminus of another protein such as TPO. Such a fusion is termed an "Fc-X" fusion, where X is a ligand (such as TPO) and Fc-X proteins have a number of distinctive, advantageous biological properties. In particular, whereas such fusion proteins can still bind the relevant Fc receptors on cell surfaces, when the ligand binds to its receptor, the orientation of the Fc region is altered such that antibody-dependent cell-mediated cytotoxicity and complement fixation are activated by the sequences present in the Fc domain.

The term "immunoglobulin" is used herein to refer to a protein consisting of one or more polypeptides substantially encoded by immunoglobulin genes. The recognised immunoglobulin genes include the kappa, lambda, alpha, gamma (IgG1, IgG2, IgG3, IgG4), sigma, epsilon, and µ constant region genes and in nature multiple immunoglobulin variable region genes.

The term Fc is used herein to refer to an immunoglobulin heavy chain constant region domain.

The term "T-cell epitope" means according to the understanding of this invention an amino acid sequence which is able to bind MEC class II, able to stimulate T-cells and/or also to bind (without necessarily measurably activating) T-cells in complex with MHC class II.

Reference to "substantially non-immunogenic" or "reduced immunogenic potential" includes reduced immunogenicity compared to a parent protein or to a fusion protein containing the wild-type (WT) or native amino acid sequences of the test moiety.

The term "immunogenicity" includes an ability to provoke, induce or otherwise facilitate a humoral and or T-cell mediated response in a host animal and in particular where the "host animal" is a human.

The terms "T-cell assay" and "immunogenicity assay" concern ex vivo measures of immune reactivity. As such these involve a test immunogen e.g. a protein or peptide being brought into contact with live human immune cells and their reactivity measured. A typical parameter of induced reactivity is proliferation. The presence of suitable control determinations are critical and implicit in the assay.

"Time course assay" refers to a biological assay such as a proliferation assay in which determinations of activity are made sequentially over a period of time. In the present context, a "time course T-cell assay", refers to the determination of T-cell proliferation in response to a test immunogen (peptide) at multiple times following exposure to the test immunogen. The terms "time course T-cell assay" and "time course immunogenicity assay" may be used interchangeably herein.

One conventional way in which T-cell assays are expressed is by use of a "stimulation index" or "SI". The stimulation index (SI) is conventionally derived by division of the proliferation score (e.g. counts per minute of radioactivity if using for example $^3$H-thymidine incorporation) measured to a test immunogen such as a peptide by the score measured in cells not contacted with a test immunogen. Test immunogens (peptides) which evoke no response give SI=1.0 although in practice SI values in the range 0.8-1.2 are unremarkable. The inventors have established that in the operation of such immunogenicity assays, a stimulation index equal to or greater than 2.0 is a useful measure of significant induced proliferation.

PBMC means peripheral blood mononuclear cells in particular as obtained from a sample of blood from a donor. PBMC are readily isolated from whole blood samples using a density gradient centrifugation technique well understood in the art and comprise predominantly lymphocytes (B and T cells) and monocytes. Other cell types are also represented.

"Relative activity" means according the present context activity measured for a test protein in any single assay expressed relative to the activity measured for a positive control protein in an identical assay and usually conducted in parallel. Thus if the test protein and the control protein have the same measured activity the relative activity is said to be 1.

A "proliferation assay" according to the present context means a biological assay able to provide a reading of the functional capability of the test protein. In the present instance this means the ability of a given TPO mutein or TPO fusion protein to evoke a specific measurable proliferative response in a live cell. Particularly suitable proliferation assays are exemplified herein using TF-1 cells or M0-e7 cells. Other cells and assay formats can be contemplated to also provide quantitative estimations of specific activity of the test molecules and permit $ED_{50}$ determinations.

In another aspect, the present invention relates to nucleic acids encoding modified TPO entities. Such nucleic acids are preferably comprised within an expression vector. The control sequences that are suitable for prokaryotes, for example, include a promoter, optionally an operator sequence, and a ribosome binding site. Eukaryotic cells are known to utilise promoters, enhancers and polyadenylation signals. Such nucleic acids in general comprise a selection means typically an additional gene encoding a protein able to provide for the survival of the host cell. An example of such a selection gene is the beta-lactamase gene suitable for some E. coli host cells and this and others are well known in the art ["Molecular Cloning: A Laboratory Manual", second edition (Sambrook et al., 1989); "Gene Transfer Vectors for Mammalian Cells" (J. M. Miller & M. P. Calos, eds., 1987); "Current Protocols in Molecular Biology" (F. M. Ausubel et al., eds., 1987)].

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in the same reading frame. However, enhancers do not have to be contiguous. Linking is accomplished by ligation at convenient restriction sites. If such sites do not exist, the synthetic oligonucleotide adaptors or linkers are used in accordance with conventional practice.

In some embodiments the expression vector comprises a nucleic acid sequence encoding a TPO variant operably linked to an expression control sequence. In various embodiments the expression vector comprises a nucleic acid sequence encoding a TPO protein selected from the group comprising inclusively M1 to M68. Such an expression vector will comprise at least the TPO encoding domain of one of the said proteins operably linked with suitable expression control and selection sequences. Such an expression vector would include degenerate versions of the nucleic acid wherein degeneracy in relation to polynucleotides refers to the fact well recognised that in the genetic code many amino acids are specified by more than one codon. The degeneracy of the code accounts for 20 different amino acids encoded by 64 possible triplet sequences of the four different bases comprising DNA.

Another aspect of the present invention is a cultured cell comprising at least one of the above-mentioned vectors.

A further aspect of the present invention is a method for preparing the modified TPO comprising culturing the above mentioned cell under conditions permitting expression of the TPO from the expression vector and purifying the TPO from the cell.

In a yet further aspect, the present invention relates to methods for therapeutic treatment of humans using the TPO compositions. For administration to an individual, any of the modified compositions would be produced to be preferably at least 80% pure and free of pyrogens and other contaminants. It is further understood that the therapeutic compositions of the TPO proteins may be used in conjunction with a pharmaceutically acceptable excipient. The pharmaceutical compositions according to the present invention are prepared conventionally, comprising substances that are customarily used in pharmaceuticals, e.g. Remington's Pharmaceutical Sciences, (Alfonso R. Gennaro ed. 18$^{th}$ edition 1990), including excipients, carriers adjuvants and buffers. The compositions can be administered, e.g. parenterally, enterally, intramuscularly, subcutaneously, intravenously or other routes useful to achieve an effect. Conventional excipients include pharmaceutically acceptable organic or inorganic carrier substances suitable for parenteral, enteral and other routes of administration that do not deleteriously react with the agents. For parenteral application, particularly suitable are injectable sterile solutions, preferably oil or aqueous solutions, as well as suspensions, emulsions or implants, including suppositories. Ampules are convenient unit dosages. The pharmaceutical preparations can be sterilised and, if desired, mixed with stabilisers, wetting agents, emulsifiers, salts for influencing osmotic pressure, buffers or other substances that do not react deleteriously with the active compounds.

The major embodiments of the present invention are encompassed by the TPO protein sequences M1-M67 and the fusion protein sequences F-M1 to F-M67, or F-L-M1 to F-L-M67, or F1-L1-M1 to F1-L1-M67. The proteins are fusion proteins of the type "Fc-X" wherein X in this present instance comprise TPO muteins. The TPO proteins are expressed in mammalian cell-lines as a C-terminal fusion partner, linked to the Fc unit of human $IgG_4$. The TPO sequence is fused preferably to the C-terminus of a hinge modified/$C_H2/C_H3$ Fc region of human IgG$_4$ via a 15 amino acid flexible linker between the C-terminus of the $C_H3$ and the N-terminus of TPO. The TPO domain comprises only residues 1-174 of the native counterpart. The amino acid sequence of the linker was as follows: (G)$_4$S(G)$_4$S(G)$_3$SG (SEQ ID NO: 5). The expressed fusion protein had a stoichiometry of (hinge-$C_H2$—$C_H3$-linker-TPO$_{(1-174)}$)$_2$.

Human Fc-gamma 4 was used as the fusion partner in all preferred molecules, but it can be readily recognised that in principle other isotypes could equally be used. In the present instance, immune effector functions are not desirable for a therapeutic TPO molecule. In contrast to some other human Fc isotypes, the Fc-gamma 4 isotype does not support complement activation and antibody-dependent cell-mediated cytotoxicity (ADCC) and was therefore selected for as the most preferred fusion partner.

Where the "Fc-X" approach has been used in other molecules, such as for example Fc-IL10 and IL10-Fc, the in vivo half-life in mice was extended from minutes to greater than 30 hours [Lo K-M, et al (1998) *Protein Engineering;* 11: 495-500; Gillies S D, et al (1999) *Cancer Research;* 59: 2159-2166; Zheng X. X. et al (1995) *Journal of Immunology;* 154: 5590-5600]. Similarly, where an "X-Fc" molecule has been used as a therapeutic in humans, the serum half-life is recorded at 3 days (Korth-Bradley J M, et al (2000) *Annals of Pharmacotherapy;* 34: 161-164].

The inventors have provided TPO fusion proteins that show increased activity compared to the fusion proteins containing the wild-type (WT) TPO moiety. The "WT" or "native" fusion proteins constructed herein has been designated clone ID 00 (M68, F-M68. F-L-M68, F1-L1-M68).

Using a proliferation assay in TF-1 cells, the native fusion protein has been found to have an ED$_{50}$ value of around 12.0 ng/ml in some determinations and when using M0-7e cells, around 25.0 ng/ml in some determinations By contrast, it has been somewhat surprisingly found that a most preferred molecule of the invention (M1, F-M1. F-L-M1, F1-L1-M1) has an ED$_{50}$ value in TF-1 cells of around 11.5 ng/ml in some determinations and when using M0-7e cells an ED$_{50}$ of around 18.0 ng/ml. Given that this molecule is a TPO mutein, these results indicate that the changes to the sequence have had a beneficial effect on direct functional activity.

Enhanced potency in the molecule attributed to the dimeric nature of the protein by virtue of the Fc-domain is demonstrated by comparison of the ED$_{50}$ values found using the full size (non-Fc linked) human TPO molecule in TF-1 and E0-7e based proliferation assays. In the present studies, monomeric full-length recombinant human (r-hTPO) TPO achieves an ED$_{50}$ of around 29.5 ng/ml using TF-1 cells and around 70.0 ng/ml using M0-7e cells. A most preferred molecule of the invention therefore demonstrates approximately between 2.5-4.0 fold enhanced activity over r-hTPO.

A further example of an especially preferred molecule of the invention with significantly enhanced activity provided by the TPO mutein containing the substitiution set M55K, A60R, V161A (M67, F-M67. F-L-M67, F1-L1-M67). This protein is highly potent in the TF-1 assay with a relative activity of 0.4. This molecule is therefore more active even than a TPO fusion protein with a WT TPO domain (M68, F-M68.F-L-M68, F1-L1-M68).

Although the M55K, A60R, V161A (M67,F-M67.F-L-M67,F1-L1-M67) mutein is clearly a highly potent molecule, this mutein is not as active as the mutein comprising only the M55K and A60R substitutions (M66, F-M66.F-L-M66,F1-L1-M68). This mutein demonstrates a relative activity of 0.2 in the TF-1 assay.

Accordingly therefore, the TPO proteins M1, M66 and M67 including their different fusion structures as indicated above and below, are especially preferred molecules of the invention.

The TPO muteins of the present were constructed to be less immunogenic than the parental molecule. The design of individual muteins was directed from immunological considerations as well as functional activity data. Two regions of immunological importance within the N-domain of the molecule were defined using screening assays involving use of PBMC preparations from healthy donor subjects. This approach has proven to be a particularly effective method for the identification such biologically relevant immunogenic peptides and is disclosed herein as an embodiment of the invention. In the present study, the method has involved the testing of overlapping TPO-derived peptide sequences in a scheme so as to scan and test the TPO sequence comprising residues 1-177. Such a scan required synthesis and use of 55 peptides each of 15 residues in length. The synthetic peptides were tested for their ability to evoke a proliferative response in human T-cells cultured in vitro. Where this type of approach is conducted using naïve human T-cells taken from healthy donors, the inventors have established that a stimulation index equal to or greater than 2.0 is a useful measure of induced proliferation.

Two epitope regions were identified in these studies. Region 1 encompasses TPO residues 49-75 and comprises the sequence: GEWKTQMEETKAQDILGAVTLLLEGVM (SEQ ID NO: 2). Region 2 encompasses TPO residues 157-171 and comprises the sequence: PTTAVPSRTSLVLTL (SEQ ID NO: 3).

The R1 and R2 peptide sequences represent the critical information required for the construction of modified TPO molecules in which one or more of these epitopes is compromised. Equally, The R1 and R2 peptide sequences represent the critical information required for the production of tolerogenic peptides. Epitope regions R1 and R2 are each embodiments of the invention.

Under the scheme of the present, the epitopes are compromised by mutation to result in sequences no longer able to function as T-cell epitopes. It is possible to use recombinant DNA methods to achieve directed mutagenesis of the target sequences and many such techniques are available and well known in the art. Broadly, the TPO muteins herein were constructed containing mutations within the two identified immunogenic regions R1 and R2. Individual residues were targeted based upon the known binding properties of HLA-DR molecules in that they have an almost exclusive preference for a hydrophobic amino acid in pocket 1 and that this is the most important determinant of peptide binding [Jardetzky, T. S. et al (1990), *EMBO J.* 9: 1797-1803; Hill, C. M. et al (1994) *J. Immunol.* 152: 2890-2898]. Exhaustive mutational analysis identified those residues within these regions that could be altered without adversely affecting the activity of the fusion protein. Choice of alternate residue was guided comparison to other TPO proteins from other species. Buried residues were replaced with either alanine or similar sized non-hydrophobic residues whereas exposed residues were scanned with all possible non-hydrophobic alternatives.

The general method of the present invention leading to the modified TPO comprises the following steps:

(a) determining the amino acid sequence of the polypeptide or part thereof;

(b) identifying one or more potential T-cell epitopes within the amino acid sequence of the protein by any method including determination of the binding of the peptides to MHC molecules using in vitro or in silico techniques or biological assays;

(c) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays. Such sequence variants are created in such a way to avoid creation of new potential T-cell epitopes by the sequence variations unless such new potential T-cell epitopes are, in turn, modified in such a way to substantially reduce or eliminate the activity of the T-cell epitope; and (d) constructing such sequence variants by recombinant DNA techniques and testing said variants in order to identify one or more variants with desirable properties according to well known recombinant techniques.

Taken together, the inventors have been able to define improved TPO proteins which can be depicted by the following structure (M):

SPAPPACDLRVLSKLLRDSHVLHSRLSQCPEVHPLPTPVLLPAVDFSLG
$X^1X^2$KTQX$^3$EEX$^4$KX$^5$X$^6$DX$^7$LGAX$^8$TX$^9$LX$^{10}$X$^{11}$GVMAARGQLGPTCL
SSLLGQLSGQVRLLLGALQSLLGTQLPPQGRTTAHKDPNAIFLSFQHLLR
GKVRFLMLVGGSTLCVRRAPPTTAX$^{12}$X$^{13}$SRTSLVLTLNEL
(SEQ ID NO: 1), wherein
 $X^1$ is A, E;
 $X^2$ is S, W;
 $X^3$ is A or T or K, S or M;
 $X^4$ is A, T;
 $X^5$ is R, A;
 $X^6$ is A or T or Q;
 $X^7$ is A or T or I;
 $X^8$ is A or T or V;
 $X^9$ is A or T or S or L;
 $X^{10}$ is A or L;
 $X^{11}$ is A or S or E;
 $X^{12}$ is N or A or T or R or E or D or G or H or P or K or Q or V;
 $X^{13}$ is A or P,
 and whereby simultaneously $X^1$=E, $X^2$=W, $X^3$=M, $X^4$=T, $X^5$=A, $X^6$=Q, $X^7$=I, $X^8$=V, $X^9$=L, $X^{10}$=L, $X^{11}$=E, $X^{12}$=V and $X^{13}$=P are excluded, or, alternatively, fusion proteins of the structure:

F-(L)n-M, wherein M has the meaning as specified above, F is an immunoglobulin heavy chain constant region, preferably an Fc portion, and L is an optional linker molecule (n=0, 1), preferably a peptide linker having 4-20 amino acid residues. Preferably the Fc region derives from human IgG4 an may be linked at its N-terminal to a hinge region, which may be modified in order to reduce immunogenicity or to improve other desired properties.

The following, figures, sequence listing and examples are provided to aid the understanding of the present invention. It is understood that modifications can be made in the procedures set fourth without departing from the spirit of the invention.

DESCRIPTION OF THE SEQUENCES

To aid the understanding of the invention, Table 1 below sets out a description of the fusion protein TPO muteins. The derivation and properties of these proteins are also more fully disclosed in the examples. In Table 1 the column heading labeled "Substitution(s)" refers to substitutions in SEQ ID NO: 4, i.e., native human TPO.

TABLE 1

| Clone ID | Substitution(s)* | F1-L1-M Sequence No. |
| --- | --- | --- |
| 37101 | A60R, V161A | M1 |
| 1394867 | I63A, V67T, V161N, P162A | M2 |
| 12394867 | I63T, V67A, V161N, P162A | M3 |
| 1374972 | M55A, I63A, V67A, V161A | M4 |
| 1374973 | M55T, I63A, V67A, V161A | M5 |
| 12484973 | M55T, I63T, V67A, V161A | M6 |
| 1374968 | Q61A, I63A, V67A, V161A | M7 |
| 12484968 | Q61A, I63T, V67A, V161T | M8 |
| 124849 | I63T, V67A, V161T | M9 |
| 123749 | I63T, V67A, V161A | M10 |
| 13749 | I63A, V67A, V161A | M11 |
| 14849 | I63A, V67A, V161T | M12 |
| 124860 | I63T, V67T, V161T | M13 |
| 3849 | V67A, V161R | M14 |
| 4849 | V67A, V161T | M15 |
| 3760 | V67T, V161A | M16 |
| 4860 | V67T, V161T | M17 |
| 3749 | V67A, V161A | M18 |
| 4249 | V67A, V161E | M19 |
| 1248 | I63T, V161T | M20 |
| 1238 | I63T, V161R | M21 |
| 1242 | I63T, V161E | M22 |
| 1237 | I63T, V161A | M23 |
| 149 | I63A, V67A | M24 |
| 160 | I63A, V67T | M25 |
| 1249 | I63T, V67A | M26 |
| 137 | I63A, V161A | M27 |
| 142 | I63A, V161E | M28 |
| 138 | I63A, V161R | M29 |
| 148 | I63A, V161T | M30 |
| 6063 | E50A, V67T | M31 |
| 163 | E50A, I63A | M32 |
| 1263 | E50A, I63T | M33 |
| 4263 | E50A, V161E | M34 |
| 37 | V161A | M35 |
| 40 | V161D | M36 |
| 42 | V161E | M37 |
| 43 | V161G | M38 |
| 44 | V161H | M39 |
| 39 | V161N | M40 |
| 46 | V161P | M41 |
| 45 | V161K | M42 |
| 41 | V161Q | M43 |
| 38 | V161R | M44 |
| 48 | V161T | M45 |
| 49 | V67A | M46 |
| 60 | V67T | M47 |
| 1 | I63A | M48 |
| 12 | I63T | M49 |
| 68 | Q61A | M50 |
| 69 | Q61T | M51 |
| 72 | M55A | M52 |
| 102 | M55K | M53 |
| 74 | M55S | M54 |
| 73 | M55T | M55 |
| 100 | T58A | M56 |
| 35 | W51S | M57 |
| 63 | E50A | M58 |

TABLE 1-continued

| Clone ID | Substitution(s)* | F1-L1-M Sequence No. |
|---|---|---|
| 77 | L69A | M59 |
| 78 | L69S | M60 |
| 79 | L69T | M61 |
| 83 | L71A | M62 |
| 86 | E72A | M63 |
| 87 | E72S | M64 |
| 101 | A60R | M65 |

TABLE 1-continued

| Clone ID | Substitution(s)* | F1-L1-M Sequence No. |
|---|---|---|
| 101102 | M55k, A60R | M66 |
| 37101102 | M55k, A60R, V161A | M67 |
| 00 | WT | M68 |

*The residue numbering for the TPO substitutions commences from residue 1 of the TPO reading frame and is independent of any Fc component.

```
M1-M67 (modified human TPO, truncated form 1-174)

M1 (SEQ ID NO: 6):
S P A P P A C D L R V L S K L L R D S H V L H S R L S Q C P E V H P L
P T P V L L P A V D F S L G E W K T Q M E E T K R Q D I L G A V T T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M2 (SEQ ID NO: 7):
S P A P P A C D L R V L S K L L R D S H V L H S R L S Q C P E V H P L
P T P V L L P A V D F S L G E W K T Q M E E T K A Q D A L G A T T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A N A S R T S L V L T L N E L

M3 (SEQ ID NO: 8):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A N A S R T S L V L T L N E L

M4 (SEQ ID NO: 9):
S P A P P A C D L R V L S K L L R D S H V L H S R L S Q C P E V H P L
P T P V L L P A V D F S L G E W K T Q A E E T K A Q D A L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M5 (SEQ ID NO: 10):
S P A P P A C D L R V L S K L L R D S H V L H S R L S Q C P E V H P L
P T P V L L P A V D F S L G E W K T Q T E E T K A Q D A L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M6 (SEQ ID NO: 11):
S P A P P A C D L R V L S K L L R D S H V L H S R L S Q C P E V H P L
P T P V L L P A V D F S L G E W K T Q T E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A T S R T S L V L T L N E L

M7 (SEQ ID NO: 12):
S P A P P A C D L R V L S K L L R D S H V L H S R L S Q C P E V H P L
P T P V L L P A V D F S L G E W K T Q M E E T K A A D A L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M8 (SEQ ID NO: 13):
S P A P P A C D L R V L S K L L R D S H V L H S R L S Q C P E V H P L
P T P V L L P A V D F S L G E W K T Q M E E T K A A D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A T P S R T S L V L T L N E L

M9 (SEQ ID NO: 14):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A T P S R T S L V L T L N E L
```

-continued

M1-M67 (modified human TPO, truncated form 1-174)

M10 (SEQ ID NO: 15):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M11 (SEQ ID NO: 16):
S P A P P A C D L R V L S K L L R D S H V L H S R L S Q C P E V H P L
P T P V L L P A V D F S L G E W K T Q M E E T K A Q D A L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M12 (SEQ ID NO: 17):
S P A P P A C D L R V L S K L L R D S H V L H S R L S Q C P E V H P L
P T P V L L P A V D F S L G E W K T Q M E E T K A Q D A L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M13 (SEQ ID NO: 18):
S P A P P A C D L R V L S K L L R D S H V L H S R L S Q C P E V H P L
P T P V L L P A V D F S L G E W K T Q M E E T K A Q D T L G A T T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M14 (SEQ ID NO: 19):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M15 (SEQ ID NO: 20):
S P A P P A C D L R V L S K L L R D S H V L H S R L S Q C P E V H P L
P T P V L L P A V D F S L G E W K T Q M E E T K A Q D I L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M16 (SEQ ID NO: 21):
S P A P P A C D L R V L S K L L R D S H V L H S R L S Q C P E V H P L
P T P V L L P A V D F S L G E W K T Q M E E T K A Q D I L G A T T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M17 (SEQ ID NO: 22):
S P A P P A C D L R V L S K L L R D S H V L H S R L S Q C P E V H P L
P T P V L L P A V D F S L G E W K T Q M E E T K A Q D I L G A T T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M18 (SEQ ID NO: 23):
S P A P P A C D L R V L S K L L R D S H V L H S R L S Q C P E V H P L
P T P V L L P A V D F S L G E W K T Q M E E T K A Q D I L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M19 (SEQ ID NO: 24):
S P A P P A C D L R V L S K L L R D S H V L H S R L S Q C P E V H P L
P T P V L L P A V D F S L G E W K T Q M E E T K A Q D I L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A E P S R T S L V L T L N E L

M20 (SEQ ID NO: 25):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A T P S R T S L V L T L N E L

-continued

M1-M67 (modified human TPO, truncated form 1-174)

M21 (SEQ ID NO: 26):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A R P S R T S L V L T L N E L

M22 (SEQ ID NO: 27):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A E P S R T S L V L T L N E L

M23 (SEQ ID NO: 28):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M24 (SEQ ID NO: 29):
S P A P P A C D L R V L S K L L R D S H V L H S R L S Q C P E V H P L
P T P V L L P A V D F S L G E W K T Q M E E T K A Q D A L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M25 (SEQ ID NO: 30):
S P A P P A C D L R V L S K L L R D S H V L H S R L S Q C P E V H P L
P T P V L L P A V D F S L G E W K T Q M E E T K A Q D A L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M26 (SEQ ID NO: 31):
S P A P P A C D L R V L S K L L R D S H V L H S R L S Q C P E V H P L
P T P V L L P A V D F S L G E W K T Q M E E T K A Q D T L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M27 (SEQ ID NO: 32):
S P A P P A C D L R V L S K L L R D S H V L H S R L S Q C P E V H P L
P T P V L L P A V D F S L G E W K T Q M E E T K A Q D A L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M28 (SEQ ID NO: 33):
S P A P P A C D L R V L S K L L R D S H V L H S R L S Q C P E V H P L
P T P V L L P A V D F S L G E W K T Q M E E T K A Q D A L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A E P S R T S L V L T L N E L

M29 (SEQ ID NO: 34):
S P A P P A C D L R V L S K L L R D S H V L H S R L S Q C P E V H P L
P T P V L L P A V D F S L G E W K T Q M E E T K A Q D A L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A R P S R T S L V L T L N E L

M30 (SEQ ID NO: 35):
S P A P P A C D L R V L S K L L R D S H V L H S R L S Q C P E V H P L
P T P V L L P A V D F S L G E W K T Q M E E T K A Q D A L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A T P S R T S L V L T L N E L

M31 (SEQ ID NO: 36):
S P A P P A C D L R V L S K L L R D S H V L H S R L S Q C P E V H P L
P T P V L L P A V D F S L G E W K T Q M E E T K A Q D I L G A T T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

-continued

M1-M67 (modified human TPO, truncated form 1-174)

M32 (SEQ ID NO: 37):
S P A P P A C D L R V L S K L L R D S H V L H S R L S Q C P E V H P L
P T P V L L P A V D F S L G E W K T Q M E E T K A Q D A L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M33 (SEQ ID NO: 38):
S P A P P A C D L R V L S K L L R D S H V L H S R L S Q C P E V H P L
P T P V L L P A V D F S L G E W K T Q M E E T K A Q D T L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M34 (SEQ ID NO: 39):
S P A P P A C D L R V L S K L L R D S H V L H S R L S Q C P E V H P L
P T P V L L P A V D F S L G A W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A E P S R T S L V L T L N E L

M35 (SEQ ID NO: 40):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M36 (SEQ ID NO: 41):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A D P S R T S L V L T L N E L

M37 (SEQ ID NO: 42):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A E P S R T S L V L T L N E L

M38 (SEQ ID NO: 43):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A G P S R T S L V L T L N E L

M39 (SEQ ID NO: 44):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A H P S R T S L V L T L N E L

M40 (SEQ ID NO: 45):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A N P S R T S L V L T L N E L

M41 (SEQ ID NO: 46):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A P P S R T S L V L T L N E L

M42 (SEQ ID NO: 47):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A K P S R T S L V L T L N E L

M1-M67 (modified human TPO, truncated form 1-174)

M43 (SEQ ID NO: 48):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A Q P S R T S L V L T L N E L

M44 (SEQ ID NO: 49):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A R P S R T S L V L T L N E L

M45 (SEQ ID NO: 50):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A T P S R T S L V L T L N E L

M46 (SEQ ID NO: 51):
S P A P P A C D L R V L S K L L R D S H V L H S R L S Q C P E V H P L
P T P V L L P A V D F S L G E W K T Q M E E T K A Q D I L G A A T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M47 (SEQ ID NO: 52):
S P A P P A C D L R V L S K L L R D S H V L H S R L S Q C P E V H P L
P T P V L L P A V D F S L G E W K T Q M E E T K A Q D I L G A T T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M48 (SEQ ID NO: 53):
S P A P P A C D L R V L S K L L R D S H V L H S R L S Q C P E V H P L
P T P V L L P A V D F S L G E W K T Q M E E T K A Q D A L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M49 (SEQ ID NO: 54):
S P A P P A C D L R V L S K L L R D S H V L H S R L S Q C P E V H P L
P T P V L L P A V D F S L G E W K T Q M E E T K A Q D T L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M50 (SEQ ID NO: 55):
S P A P P A C D L R V L S K L L R D S H V L H S R L S Q C P E V H P L
P T P V L L P A V D F S L G E W K T Q M E E T K A A D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M51 (SEQ ID NO: 56):
S P A P P A C D L R V L S K L L R D S H V L H S R L S Q C P E V H P L
P T P V L L P A V D F S L G E W K T Q M E E T K A T D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M52 (SEQ ID NO: 57):
S P A P P A C D L R V L S K L L R D S H V L H S R L S Q C P E V H P L
P T P V L L P A V D F S L G E W K T Q A E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M53 (SEQ ID NO: 58):
S P A P P A C D L R V L S K L L R D S H V L H S R L S Q C P E V H P L
P T P V L L P A V D F S L G E W K T Q K E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

-continued

M1-M67 (modified human TPO, truncated form 1-174)

M54 (SEQ ID NO: 59):
S P A P P A C D L R V L S K L L R D S H V L H S R L S Q C P E V H P L
P T P V L L P A V D F S L G E W K T Q S E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M55 (SEQ ID NO: 60):
S P A P P A C D L R V L S K L L R D S H V L H S R L S Q C P E V H P L
P T P V L L P A V D F S L G E W K T Q T E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M56 (SEQ ID NO: 61):
S P A P P A C D L R V L S K L L R D S H V L H S R L S Q C P E V H P L
P T P V L L P A V D F S L G E W K T Q M E E A K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M57 (SEQ ID NO: 62):
S P A P P A C D L R V L S K L L R D S H V L H S R L S Q C P E V H P L
P T P V L L P A V D F S L G E S K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M58 (SEQ ID NO: 63):
S P A P P A C D L R V L S K L L R D S H V L H S R L S Q C P E V H P L
P T P V L L P A V D F S L G A W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M59 (SEQ ID NO: 64):
S P A P P A C D L R V L S K L L R D S H V L H S R L S Q C P E V H P L
P T P V L L P A V D F S L G E W K T Q M E E T K A Q D I L G A V T A L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M60 (SEQ ID NO: 65):
S P A P P A C D L R V L S K L L R D S H V L H S R L S Q C P E V H P L
P T P V L L P A V D F S L G E W K T Q M E E T K A Q D I L G A V T S L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M61 (SEQ ID NO: 66):
S P A P P A C D L R V L S K L L R D S H V L H S R L S Q C P E V H P L
P T P V L L P A V D F S L G E W K T Q M E E T K A Q D I L G A V T T L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M62 (SEQ ID NO: 67):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M63 (SEQ ID NO: 68):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M64 (SEQ ID NO: 69):
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

```
M1-M67 (modified human TPO, truncated form 1-174)
```

M65 (SEQ ID NO: 70):
S P A P P A C D L R V L S K L L R D S H V L H S R L S Q C P E V H P L
P T P V L L P A V D F S L G E W K T Q M E E T K R Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M66 (SEQ ID NO: 71):
S P A P P A C D L R V L S K L L R D S H V L H S R L S Q C P E V H P L
P T P V L L P A V D F S L G E W K T Q K E E T K R Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L

M67 (SEQ ID NO: 72):
S P A P P A C D L R V L S K L L R D S H V L H S R L S Q C P E V H P L
P T P V L L P A V D F S L G E W K T Q K E E T K R Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A A P S R T S L V L T L N E L

M68 (wild-type human TPO, truncated form 1-174)
S P A P P A C D L R V L S K L L R D S H V L H S R L S Q C P E V H P L
P T P V L L P A V D F S L G E W K T Q M E E T K A Q D I L G A V T L L
L E G V M A A R G Q L G P T C L S S L L G Q L S G Q V R L L L G A L Q
S L L G T Q L P P Q G R T T A H K D P N A I F L S F Q H L L R G K V R
F L M L V G G S T L C V R R A P P T T A V P S R T S L V L T L N E L F1 (Fc domain of human IgG4 including modified hinge region)
E P K S S D K T H T C P P C P A P E F L G G P S V F L F P P K P K D T L M I
S R T P E V T C V V V D V S Q E D P E V Q F N W Y V D G V E V H N A K T K P
R E E Q F N S T Y R V V S V L T V L H Q D W L N G K E Y K C K V S N K G L P
S S I E K T I S K A K G Q P R E P Q V Y T L P P S Q E E M T K N Q V S L T C
L V K G F Y P S D I A V E W E S N G Q P E N N Y K T T P P V L D S D G S F F
L Y S K L T V D K S R W Q Q G N I F S C S V M H E A L H N H Y T Q K S L S L
S P G A L1 (Linker peptide)
G G G G S G G G G S G G G S G Examples of fusion proteins F-M of the present invention (in which F is any immunoglobulin heavy chain constant region and M is a modified TPO sequence of the invention) include the following: F - M1, F - M2, F - M3, F - M4, F - M5, F - M6, F - M7, F - M8, F - M9, F - M10, F - M11, F - M12, F - M13, F - M14, F - M15, F - M16, F - M17, F - M18, F - M19, F - M20, F - M21, F - M22, F - M23, F - M24, F - M25, F - M26, F - M27, F - M28, F - M29, F - M30, F - M31, F - M32, F - M33, F - M34, F - M35, F - M36, F - M37, F - M38, F - M39, F - M40, F - M41, F - M42, F - M43, F - M44, F - M45, F - M46, F - M47, F - M48, F - M49, F - M50, F - M51, F - M52, F - M53, F - M54, F - M55, F - M56, F - M57, F - M58, F - M59, F - M60, F - M61, F - M62, F - M63, F - M64, F - M65, F - M66, F - M67.

Examples of fusion proteins F - L - M of the present invention (in which F is any immunoglobulin heavy chain constant region, L is a linker peptide, and M is a modified TPO sequence of the invention) include the following: F - L - M1, F - L - M2, F - L - M3, F - L - M4, F - L - M5, F - L - M6, F - L - M7, F - L - M8, F - L - M9, F - L - M10, F - L - M11, F - L - M12, F - L - M13, F - L - M14, F - L - M15, F - L - M16, F - L - M17, F - L - M18, F - L - M19, F - L - M20, F - L - M21, F - L - M22, F - L - M23, F - L - M24, F - L - M25, F - L - M26, F - L - M27, F - L - M28, F - L - M29, F - L - M30, F - L - M31, F - L - M32, F - L - M33, F - L - M34, F - L - M35, F - L - M36, F - L - M37, F - L - M38, F - L - M39, F - L - M40, F - L - M41, F - L - M42, F - L - M43, F - L - M44, F - L - M45, F - L - M46, F - L - M47, F - L - M48, F - L - M49, F - L - M50, F - L - M51, F - L - M52, F - L - M53, F - L - M54, F - L - M55, F - L - M56, F - L - M57, F - L - M58, F - L - M59, F - L - M60, F - L - M61, F - L - M62, F - L - M63, F - L - M64, F - L - M65, F - L - M66, F - L - M67.

Examples of fusion proteins F1 - L1 - M of the present invention (in which F1 is the Fc portion from human IgG4, L1 is the peptide linker described above, and M is a modified TPO sequence of the invention) include the following: F1 - L1 - M1, F1 - L1 - M2, F1 - L1 - M3, F1 - L1 - M4, F1 - L1 - M5, F1 - L1 - M6, F1 - L1 - M7, F - L - M8, F1 - L1 - M9, F1 - L1 - M10, F1 - L1 - M11, F1 - L1 - M12, F1 - L1 - M13, F1 - L1 - M14, F1 - L1 - M15, F1 - L1 - M16, F1 - L1 - M17, F1 - L1 - M18, F1 - L1 - M19, F1 - L1 - M20, F1 - L1 - M21, F1 - L1 - M22, F1 - L1 - M23, F1 - L1 - M24, F1 - L1 - M25, F1 - L1 - M26, F1 - L1 - M27, F1 - L1 - M28, F1 - L1 - M29, F1 - L1 - M29, F1 - L1 - M30, F1 - L1 - M31, F1 - L1 - M32, F1 - L1 - M33, F1 - L1 - M34, F1 - L1 - M35, F1 - L1 - M36, F1 - L1 - M37, F1 - L1 - M38, F1 - L1 - M39, F1 - L1 - M40, F1 - L1 - M41, F1 - L1 - M42, F1 - L1 - M43, F1 - L1 - M44, F1 - L1 - M45, F1 - L1 - M46, F1 - L1 - M47, F1 - L1 - M48, F1 - L1 - M49, F1 - L1 - M50, F1 - L1 - M51, F1 - L1 - M52, F1 - L1 - M53, F1 - L1 - M54, F1 - L1 - M55, F1 - L1 - M56, F1 - L1 - M57, F1 - L1 - M58, F1 - L1 - M59, F1 - L1 - M60, F1 - L1 - M61, F1 - L1 - M62, F1 - L1 - M63, F1 - L1 - M64, F1 - L1 - M65, F1 - L1 - M66, F1 - L1 - M67.

A fusion protein with wild-type human TPO (M68) is: F1 - L1 - M68.

Figure 1:
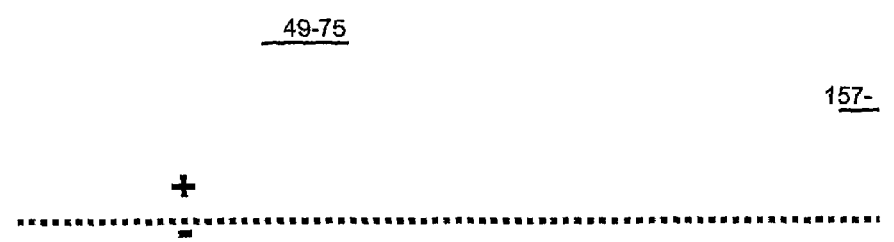
FIG. 1.
Figure 1:
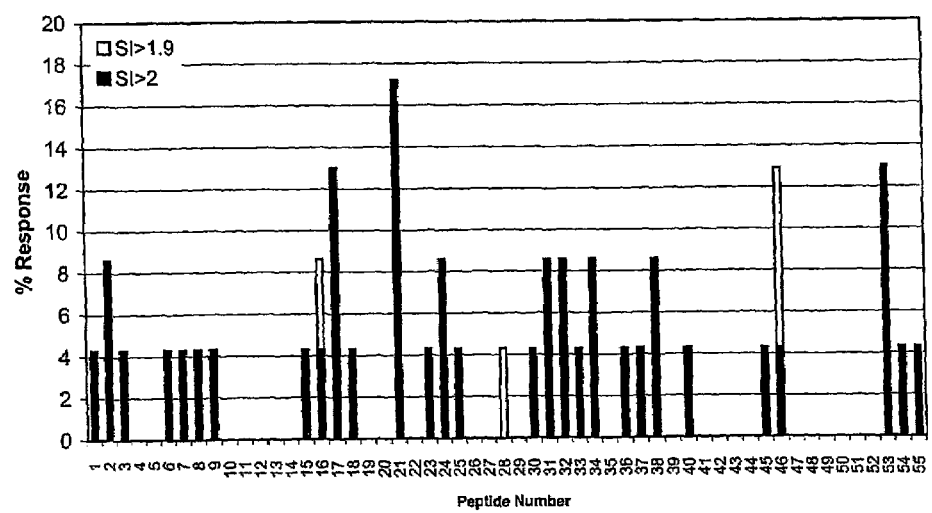

Identification of T cell epitopes in TPO (1-174). (A) 20 healthy donors were tested for reactivity with 55 overlapping (by 12 amino acids) 15 mer peptides derived from the TPO sequence. Donors that responded to peptides with an SI>2 were analyzed further by plotting the frequency of donor responses to each peptide. Prominent regions of immunogenicity are labeled according to the amino acid residue number in the TPO linear sequence and were determined by peptides that induced responses in 10% of donors; however, borderline responses where individual SI values>1.95 (two tone black and white bars) were achieved and if two (or more) adjacent peptides induced responses in 5% of donors (Region 1). (B) The mature sequence of TPO (SEQ ID NO: 4) with regions of immunogenicity boxed and highlighted in bold.

FIG. 2:

Frequency of observed responses with an SI>2 at any time point from cohorts of 20 healthy donors to either wild type region 1 and modified region 1 peptides (A); or wild type region 2 and modified region 2 peptides (B).

FIG. 3:

Immunogenicity of TPO variant peptides. Two cohorts of 20 healthy donors were used to test the immunogenicity of either wild type region 1 and modified region 1 peptides (A) or wild type region 2 and modified region 2 peptides (B). Proliferation of PBMC was assessed by tritiated thymidine incorporation on days 6, 7, 8 and 9 post-stimulation and stimulation indexes were calculated.

FIG. 4:

Mutein clone ID 102 (M53/F1-L1-M53) comprising single amino acid substitution M55K shows greater activity in a functional assay than either the WT counterpart or a control TPO preparation lacking the Fc domain. Functional activity is plotted as CPM measued using the proliferation assay (Example 4) versus concentration of TPO protein added. Proliferation was measured in TF-1 cells using culture supernatants from TPO mutein and TPO WT transfected HEK.293 cells. Supernatants were quantified by Fc ELISA and diluted to 320 ng/ml. The activity was titrated in 2 fold serial dilutions.

EXPERIMENTAL EXAMPLES

Example 1

Construction of Fc-TPO Muteins

The modified TPO proteins of the present invention were made using conventional recombinant DNA techniques. The N-terminal domain of the protein was cloned comprising residues 1-174. The coding sequence for TPO (1-174) was cloned from human human liver cDNA library using PCR. The wild-type gene was used both as a control reagent and a template from which to derive modified TPO proteins by site directed mutagenesis. WT and modified genes were inserted into a modified version of the expression vector pdC-huFc [K.-M. Lo et al., (1998) Protein Eng 11:495-500]. The TPO gene was excised with XmaI and XhoI and cloned into a similarly cut preparation of the vector which had been modified such that the TPO sequence is fused to the C-terminus of a hinge modified/$C_H2/C_H3$ Fc region of human IgG$_4$ via a 15 amino acid flexible linker between the C-terminus of the $C_H3$ and the N-terminus of TPO$_{(1-174)}$. The amino acid sequence of the linker was as follows: (G)$_4$S(G)$_4$S(G)$_3$SG (SEQ ID NO: 5). The expressed fusion protein had a stoichiometry of (hinge-$C_H2$—$C_H3$-linker-TPO$_{(1-174)}$)$_2$. The final construct used in this study was designated Fc-gamma 4-linker-TPO (clone ID 00, M68/F1-L1-M68).

DNA sequencing was conducted on all constructs. This was diligently performed to confirm introduction of desired substitutions and establish that no extraneous (undesired) substitutions had been introduced for example by PCR error.

Variants of TPO$_{(1-174)}$ linked to the Fc portion of human IgG$_4$ were constructed containing mutations within the two immunogenic regions of this domain of the protein. Desired substitutions were introduced into the TPO sequence by overlap PCR using HiFi Expand polymerase. Cycles of mutational analysis involving construction and function testing identified those residues within these regions that could be altered without adversely affecting the activity of the Fc-linked protein. The proliferation assay as described herein (see Example 4) was the main screening tool in this aspect, a total of 667 different muteins in TPO were identified with positive functional activity (Table 2).

Example 2

Transfection and Purification of Fusion Proteins

Transient transfections were done using HEK293 (ATCC# CRL-1573) cells and Lipofectamine 2000 (Invitrogen, Paisley, UK) as described by the manufacturer. Stable transfectants were also made in HEK293 cells and selected in media containing increasing concentrations of methotrexate. All cell-lines were maintained in DMEM plus 10% FBS with antibiotics and antimycotics. Fusion proteins were purified via Prosep-A chromatography followed by size exclusion chromatography (SEC). Briefly, 1 ml Prosep®-A columns (Millipore, Watford, UK) were equilibrated in PBS pH 7.4 before being loaded with 0.2 µM filtered cell-culture supernatants (up to 500 ml) that had been pH adjusted with ⅟₂₀ vols. 1M Tris-HCl pH 7.4. The column was washed with 50 ml PBS pH 7.4 and the fusion protein eluted with 0.1M citrate buffer pH 3.0 and 0.9 ml fractions collected. The fractions were immediately neutralized with 0.1 ml 1M Tris-HCl pH 8.0. SEC was done with Superdex 200 (Amersham Pharmacia, Amersham, UK) in a 3.2/30 column equilibrated and run in PBS pH 7.4 containing 0.1% Tween 80. Fractions spanning the major peak were pooled and fusion proteins quantified using molar extinction coefficients at 280 nm calculated using Lasergene™ software (Dnastar, Madison, Wis., USA). The concentrations were confirmed using a BCA protein assay (Pierce, Chester, UK).

Example 3

Quantitation of Fusion Proteins in Cell-Culture Supernatants

Fusion proteins were quantified by detecting the amount of human IgG$_4$ Fc in an ELISA format as follows: ELISA plates (Dynex Immulon4) were coated with a mouse monoclonal anti-human IgG Fc specific antibody at a dilution of 1/1500 in PBS pH7.4, 100 µl/well, for 2 h at 37° C. The plate was washed ×4 with 100 µl/well PBS/0.05% Tween 20. Human IgG standards (The Binding Site, Birmingham, UK) were diluted to 2 µg/ml in PBS/2% BSA and duplicate two-fold dilutions made vertically down the plate. Test samples were diluted 1/100 and 1/500 in PBS/2% BSA and assayed in duplicate. The plate was incubated for 1 h at room temperature and washed as before. Detection was done using 100 µl/well goat anti-human IgG Fc-specific peroxidase conjugate (The Binding Site, Birmingham, UK) at a dilution of 1/1000 in PBS, the plate washed as before and colour developed using SigmaFast OPD, 100 µl/well (Sigma, Poole, UK).

The colour reaction was stopped by the addition of 50 µl 2M sulphuric acid and the absorbance measured at 492 nm in an Anthos HTII plate reader.

Example 4

Functional Activity of Fc-TPO Muteins

The functional activity of the Fc-TPO proteins was compared using proliferation assay using either the erythro leukaemia cell line TF-1, or the megakaryocytic cell line M0-7e [Avanzi G C et al (1988) *British Journal of Haematology;* 69: 359-366; Jagerschmidt A, et al (1998) *Biochemical Journal;* 333: 729-734 and Quentmeier H, et al (1996) *Leukemia;* 10:297-310]. Cells were grown in RPMI-1640 (Invitrogen, Paisley, UK) with 10% serum supreme (Biowhittaker, Wokingham, UK), penicllin/streptomycin (Invitrogen, Paisley, UK), and GM-CSF (Peprotech, London, UK) at 2 ng/ml for TF-1 and 10 ng/ml for M0-7e.

For the assay, exponentially growing TF-1 or M0-7e cells were seeded into 96 well plates at a concentration of $2 \times 10^4$ cells per well, in assay medium supplemented with increasing amounts of conditioned medium from HEK293 cells transfected with the vector containing the protein of interest. Recombinant TPO (Peprotech) with a specific activity of $1 \times 10^6$ units/mg was used as an additional positive control reagent in these assays. Assays were performed at TPO concentrations ranging from 0 to 320 ng/ml, with duplicate serial doubling dilutions of standard r-hTPO (Peprotech) and triplicate serial doubling dilutions of test protein variants in antibiotic free media, were made horizontally across a "U" bottomed 96 well plate. The plates were incubated for 96 h at 37° C. and then 1 µCi of [$^3$H]-thymidine added over night. Cells were harvested onto filter maps and then solid scintillant melted onto the mat using a hot plate. Counts per minute (CPM) were then measured using a MicroBeta Tri Lux scintillation counter. CPM vs TPO concentration was plotted and an $EC_{50}$ value determined.

A total of 67 different TPO variants demonstrated positive activity in the proliferation assay. Positive activity was taken to be a relative activity value of less than 10. Relative activity was determined by dividing the $ED_{50}$ value derived for the protein of interest by the $ED_{50}$ value derived for the control (WT) TPO fusion protein (M66/F1-L1-M66). Of these active proteins, 31 were muteins comprising a single amino acid substitution; 23 comprised 2 amino acid substitutions, 7 comprised 3 amino acid substitutions and 7 comprised four amino acid substitutions. The sequence of each of these active TPO muteins is provided in M1 - M67 (F1-L1-M67). The relative activities of each functioning mutein are provided in Table 2. In Table 2, the heading labled "Substitution(s)" refers to an amino acid residue substitution in SEQ ID NO: 4 (human TPO).

TABLE 2

Activity of FC-TPO variants

| Clone ID | Substitution(s) | F1-L1-M sequence | Relative Activity* (proliferation in TF-1 cells) |
|---|---|---|---|
| 37101 | A60R, V161A | M1 | 1.0 |
| 1394867 | I63A, V67T, V161N, P162A | M2 | 1.0 |
| 12394867 | I63T, V67A, V161N, P162A | M3 | 1.5 |
| 1374972 | M55A, I63A, V67A, V161A | M4 | 0.2 |
| 1374973 | M55T, I63A, V67A, V161A | M5 | 0.1 |
| 12484973 | M55T, I63T, V67A, V161A | M6 | 0.1 |
| 1374968 | Q61A, I63A, V67A, V161A | M7 | 0.4 |
| 12484968 | Q61A, I63T, V67A, V161T | M8 | 1.4 |
| 124849 | I63T, V67A, V161T | M9 | 0.4 |
| 123749 | I63T, V67A, V161A | M10 | 1.0 |
| 13749 | I63A, V67A, V161A | M11 | 0.5 |
| 14849 | I63A, V67A, V161T | M12 | 1.0 |
| 124860 | I63T, V67T, V161T | M13 | 1.0 |
| 3849 | V67A, V161R | M14 | 0.6 |
| 4849 | V67A, V161T | M15 | 0.4 |
| 3760 | V67T, V161A | M16 | 0.7 |
| 4860 | V67T, V161T | M17 | 0.9 |
| 3749 | V67A, V161A | M18 | 0.2 |
| 4249 | V67A, V161E | M19 | 1.0 |
| 1248 | I63T, V161T | M20 | 0.7 |
| 1238 | I63T, V161R | M21 | 1.8 |
| 1242 | I63T, V161E | M22 | 0.4 |
| 1237 | I63T, V161A | M23 | 1.5 |
| 149 | I63A, V67A | M24 | 1.5 |
| 160 | I63A, V67T | M25 | 2.0 |
| 1249 | I63T, V67A | M26 | 1.6 |
| 137 | I63A, V161A | M27 | 3.0 |
| 142 | I63A, V161E | M28 | 1.5 |
| 138 | I63A, V161R | M29 | 3.3 |
| 148 | I63A, V161T | M30 | 4.0 |
| 6063 | E50A, V67T | M31 | 1.0 |
| 163 | E50A, I63A | M32 | 4.8 |
| 1263 | E50A, I63T | M33 | 6.3 |
| 4263 | E50A, V161E | M34 | 5.0 |
| 37 | V161A | M35 | 1.0 |
| 40 | V161D | M36 | 1.0 |
| 42 | V161E | M37 | 0.5 |
| 43 | V161G | M38 | 1.0 |
| 44 | V161H | M39 | 1.0 |
| 39 | V161N | M40 | 1.0 |
| 46 | V161P | M41 | 1.0 |
| 45 | V161K | M42 | 3.3 |
| 41 | V161Q | M43 | 1.0 |
| 38 | V161R | M44 | 2.0 |
| 48 | V161T | M45 | 1.0 |
| 49 | V67A | M46 | 0.5 |
| 60 | V67T | M47 | 0.6 |
| 1 | I63A | M48 | 2.0 |
| 12 | I63T | M49 | 2.0 |
| 68 | Q61A | M50 | 0.6 |
| 69 | Q61T | M51 | 2.3 |
| 72 | M55A | M52 | 0.3 |
| 102 | M55K | M53 | 0.1 |
| 74 | M55S | M54 | 1.0 |
| 73 | M55T | M55 | 0.1 |
| 100 | T58A | M56 | 1.0 |
| 35 | W51S | M57 | 8.0 |
| 63 | E50A | M58 | 1.0 |
| 77 | L69A | M59 | 1.0 |
| 78 | L69S | M60 | 0.7 |
| 79 | L69T | M61 | 0.2 |
| 83 | L71A | M62 | 1.8 |
| 86 | E72A | M63 | 1.8 |
| 87 | E72S | M64 | 2.1 |
| 101 | A60R | M65 | 1.4 |
| 101102 | M55K, A60R | M66 | 0.2 |
| 37101102 | M55K, A60R, V161A | M67 | 0.4 |
| 00 | WT | M68 | — |

*Relative activity is $ED_{50}$ test protein (M1–M67)/$ED_{50}$ Fc-TPO WT (M68). $ED_{50}$ measured in TF-1 cells.

Example 5

Identification of T-Cell Epitopes in Human TPO

All blood samples used in this study were obtained with approval of the Addenbrooke's Hospital Local Research Ethics Committee. T-cell epitope mapping was performed using human PBMCs isolated from blood obtained from the National Blood Transfusion Service (Addenbrooke's Hospital, Cambridge, UK). PBMCs from 20 healthy donors were isolated by Ficoll density centrifugation and stored under liquid nitrogen. Each donor was tissue-typed using an Allset™ PCR based tissue-typing kit (Dynal) and T cell assays were performed by selecting donors according to individual MHC haplotypes. 15 mer peptides staggered by three amino acids and spanning the human TPO sequence between residues 1-177 were purchased from Pepscan Systems BV (NL). Using this scheme, total of 55 peptides were required to scan the TPO residues of interest. The sequence and peptide number of these peptides are provided in Table 3.

TABLE 3

Peptides used to map immunogenic epitopes within TPO (Peptides span TPO residues 1-177)

| Peptide No | Peptide sequence | SEQ ID NO: |
|---|---|---|
| 1 | SPAPPACDLRVLSKL | 74 |
| 2 | PPACDLRVLSKLLRD | 75 |
| 3 | CDLRVLSKLLRDSHV | 76 |
| 4 | RVLSKLLRDSHVLHS | 77 |
| 5 | SKLLRDSHVLHSRLS | 78 |
| 6 | LRDSHVLHSRLSQCP | 79 |
| 7 | SHVLHSRLSQCPEVH | 80 |
| 8 | LHSRLSQCPEVHPLP | 81 |
| 9 | RLSQCPEVHPLPTPV | 82 |
| 10 | QCPEVHPLPTPVLLP | 83 |
| 11 | EVHPLPTPVLLPAVD | 84 |
| 12 | PLPTPVLLPAVDFSL | 85 |
| 13 | TPVLLPAVDFSLGEW | 86 |
| 14 | LLPAVDFSLGEWKTQ | 87 |
| 15 | AVDFSLGEWKTQMEE | 88 |
| 16 | FSLGEWKTQMEETKA | 89 |
| 17 | GEWKTQMEETKAQDI | 90 |
| 18 | KTQMEETKAQDILGA | 91 |
| 19 | MEETKAQDILGAVTL | 92 |
| 20 | TKAQDILGAVTLLLE | 93 |
| 21 | QDILGAVTLLLEGVM | 94 |
| 22 | LGAVTLLLEGVMAAR | 95 |
| 23 | VTLLLEGVMAARGQL | 96 |
| 24 | LLEGVMAARGQLGPT | 97 |
| 25 | GVMAARGQLGPTCLS | 98 |
| 26 | AARGQLGPTCLSSLL | 99 |
| 27 | GQLGPTCLSSLLGQL | 100 |
| 28 | GPTCLSSLLGQLSGQ | 101 |
| 29 | CLSSLLGQLSGQVRL | 102 |
| 30 | SLLGQLSGQVRLLLG | 103 |
| 31 | GQLSGQVRLLLGALQ | 104 |
| 32 | SGQVRLLLGALQSLL | 105 |
| 33 | VRLLLGALQSLLGTQ | 106 |
| 34 | LLGALQSLLGTQLPP | 107 |
| 35 | ALQSLLGTQLPPQGR | 108 |
| 36 | SLLGTQLPPQGRTTA | 109 |
| 37 | GTQLPPQGRTTAHKD | 110 |
| 38 | LPPQGRTTAHKDPNA | 111 |
| 39 | QGRTTAHKDPNAIFL | 112 |
| 40 | TTAHKDPNAIFLSFQ | 113 |
| 41 | HKDPNAIFLSFQHLL | 114 |
| 42 | PNAIFLSFQHLLRGK | 115 |
| 43 | IFLSFQHLLRGKVRF | 116 |
| 44 | SFQHLLRGKVRFLML | 117 |
| 45 | HLLRGKVRFLMLVGG | 118 |
| 46 | RGKVRFLMLVGGSTL | 119 |
| 47 | VRFLMLVGGSTLCVR | 120 |
| 48 | LMLVGGSTLCVRRAP | 121 |
| 49 | VGGSTLCVRRAPPTT | 122 |
| 50 | STLCVRRAPPTTAVP | 123 |
| 51 | CVRRAPPTTAVPSRT | 124 |
| 52 | RAPPTTAVPSRTSLV | 125 |
| 53 | PTTAVPSRTSLVLTL | 126 |
| 54 | AVPSRTSLVLTLNEL | 127 |
| 55 | SRTSLVLTLNELPNR | 128 |

For each donor sample, PBMCs were thawed and resuspended in AIM-V (Invitrogen) containing 100 units/ml penicillin, 100 ug/ml streptomycin and 1 mM glutamine. Triplicate cultures of $2\times10^5$ PBMC/well of flat-bottomed 96 well plate were incubated with peptides at a final concentration of 1 µM and 10 µM. Cells were incubated for 7 days before pulsing with 1 µCi/well tritiated thymidine for 18 hours. Cultures were harvested onto glass fibre filter mats using a Tomtec Mach III plate harvester and cpm values determined by scintillation counting using a Wallac Microbeta TriLux plate reader.

The results of these assays are depicted in FIG. 1. Regions of immunogenicity (FIG. 1A) were determined by identifying peptides that induced donors to respond with stimulation indexes≧2 and by determination of the donor response rate for each peptide. Peptides located within two separate regions were able to induce T cell proliferation. Region 1 encompasses TPO residues 49-75 and comprises the sequence: GEWKTQMEETKAQDILGAVTLLLEGVM (SEQ ID NO: 2) and equivalent to peptides 17-21. The donor responses to region 1 ranged from 13% to 17%. Region 2 encompasses TPO residues 157-171 and comprises the sequence: PTTAVPSRTSLVLTL (SEQ ID NO: 3) (peptide 53). The donor response rate to region 2 was 13% (FIG. 1B). Each donor was also tested for their ability to respond to two positive control peptides influenza haemagglutinin A amino acids 307-319 [J. I. Krieger et al. (1991) *Journal of Immunology*; 146: 2331-2340] and chlamydia HSP60 amino acids 125-140 [M. C. Cerrone et al. (1991) *Infection and Immunity*; 59: 79-90]. Keyhole limpet haemocyanin, a well documented potent T cell antigen was also used as a control.

Example 6

Analysis of Immunogenic Regions by Time-Course T-Cell Assays

Bulk cultures of 2-4×10$^6$ PBMC/well were established from 20 healthy donor samples in 24 well plates. Cells were incubated for 6 to 9 days with WT and variant peptides spanning the immunogenic regions (see Table 4). T cell proliferation was assessed by tritiated thymidine incorporation on days 6, 7, 8 and 9. Proliferation was assessed at each time point, by gently resuspending the bulk cultures and removing samples of PBMC, that were then incubated in triplicate wells of U-bottomed 96 well plate with 1 μCi/well tritiated thymidine for 18 hours as described above.

The time course assay was used to test variant peptides containing substitutions over WT. Substitutions were made at key locations where there was expectation that the substitution would prevent binding to MHC class II and therefore, subsequent T cell proliferation in the assay. Particular substitutions were made based on information from the crystal structure of the cytokine domain of TPO [Feese M. D. et al (2004) *Proc. Natl. Acad. Sci (USA)*; 101: 1816-1821] and various models of MHC class II binding motifs. The favoured mutations were large basic residues such as arginine or lysine but where structural models predicted severe affects on the protein structure we used alanine instead. For Region 2 we used four different alternatives for one locus as we only identified one important residue for mutagenesis studies in that sequence.

Peptides containing the mutations: M55K, T58R A60R, D62R, L69A, L70A were synthesised for region 1, and V161A, V161N, V161R and V161T for region 2 (Table 4).

Figure 2A:
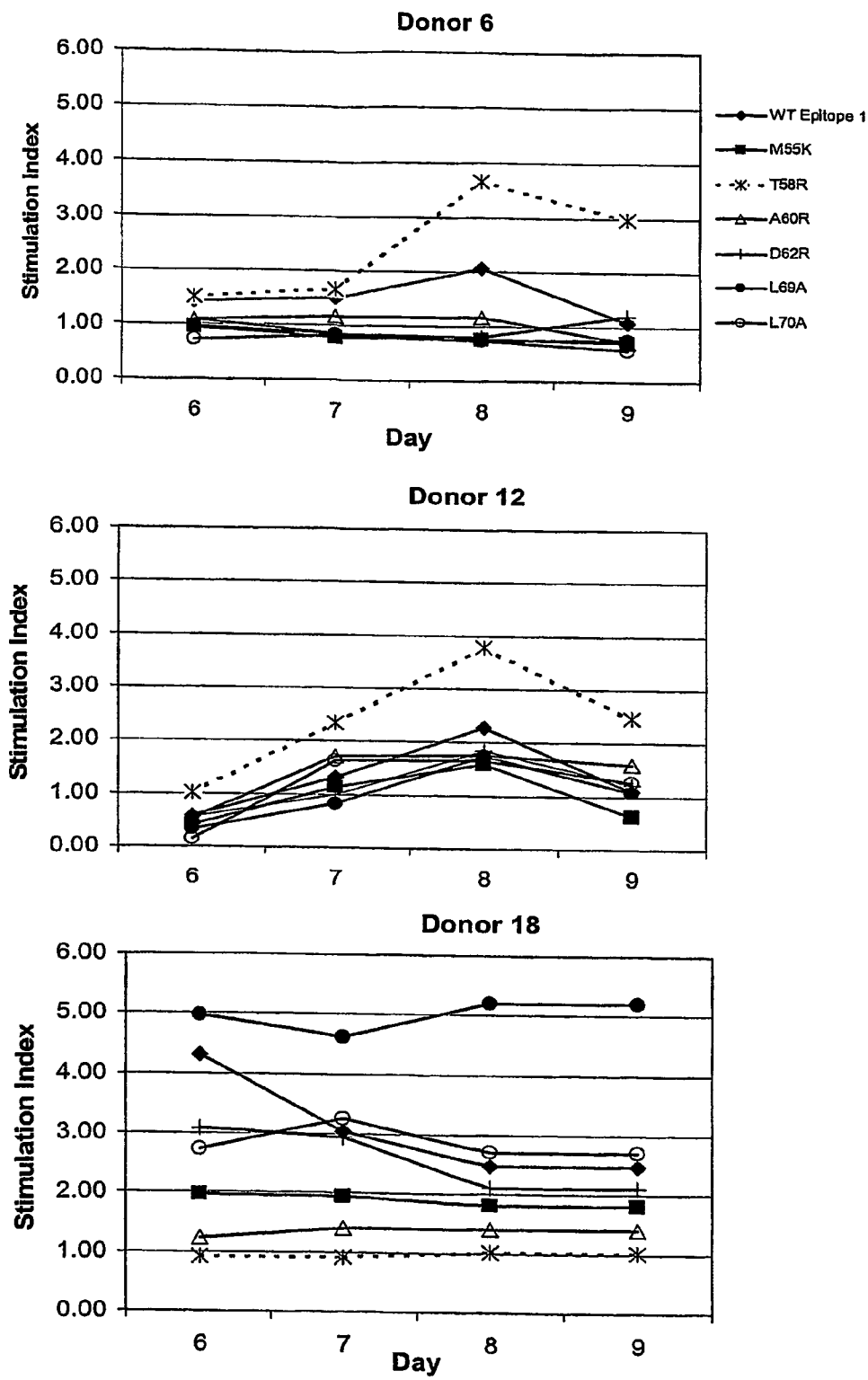
Figure 2B:
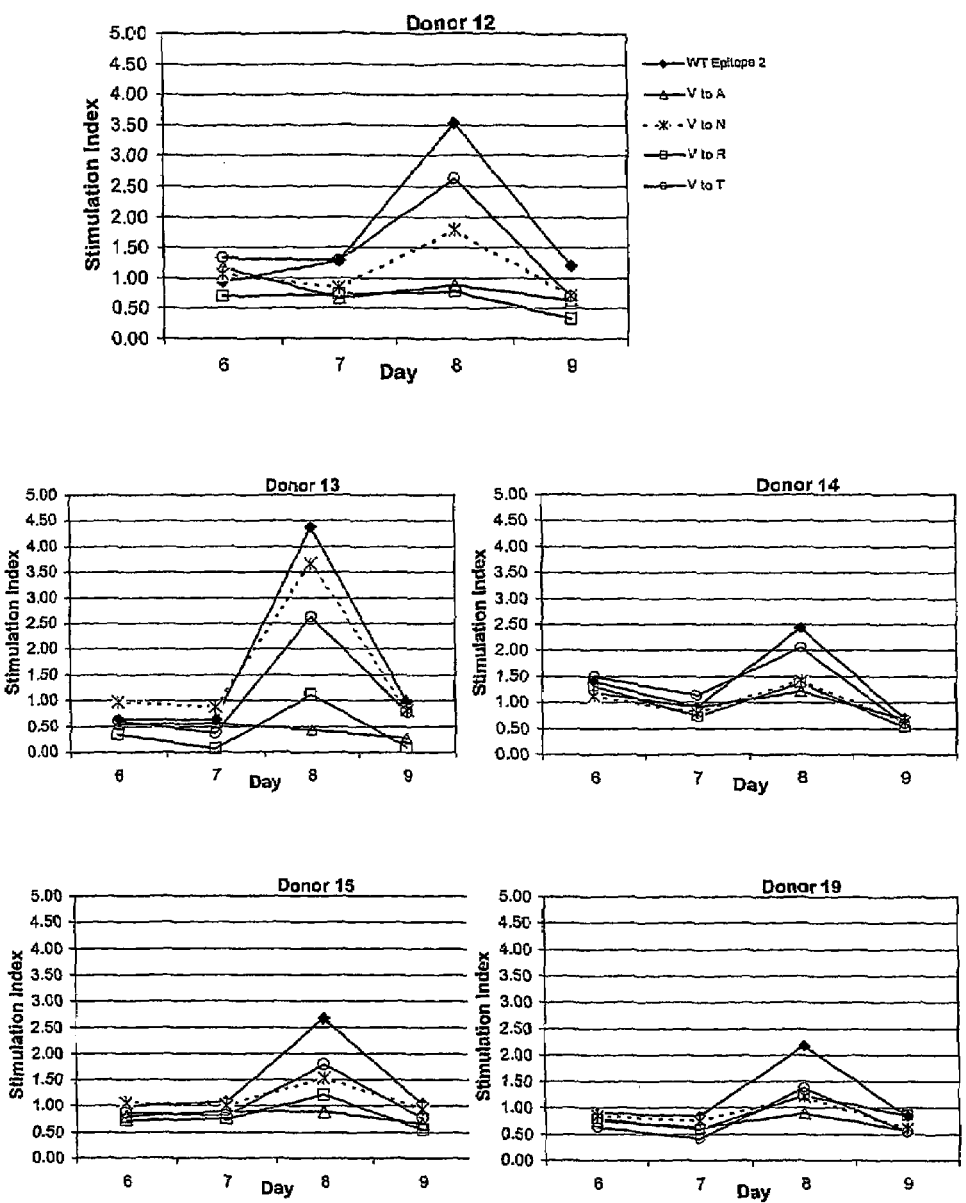
Figure 3:
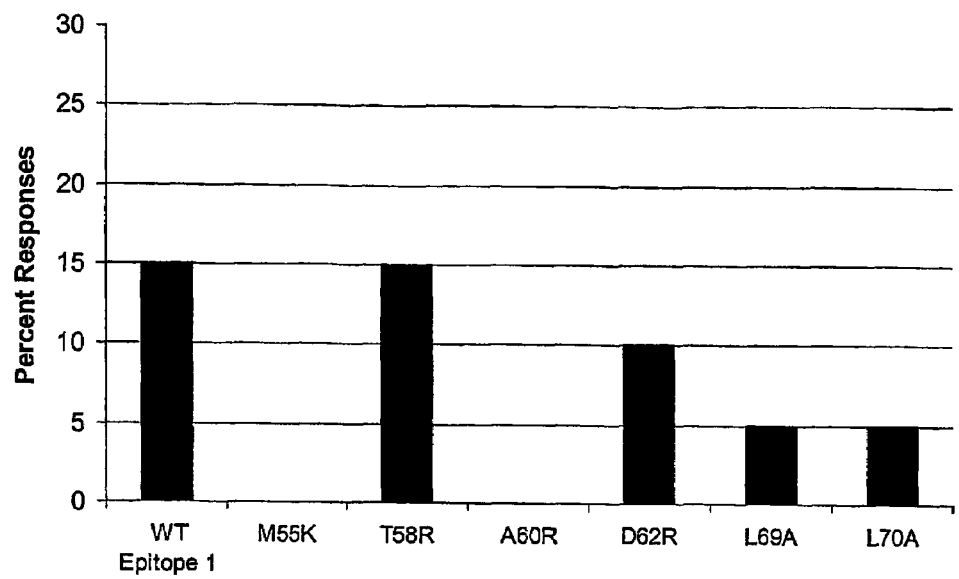
Figure 3:
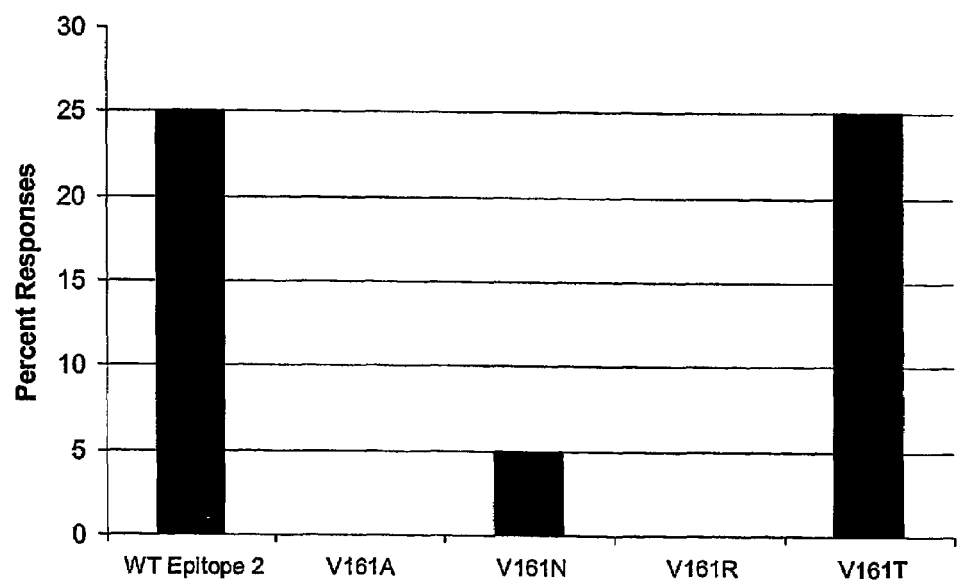

Results of this analysis are shown in FIGS. 2 and 3. FIGS. 2A and 3A show that 15% of the 20 donors responded to the original sequence region 1 sequence and T58R. By contrast none of the donors responded to the mutated sequences containing the M55K or the A60R mutations. FIGS. 2B and 3B show that 25% of the 20 donors responded to the original region 2 sequence and V161T. By contrast none of the donors responded to the mutated sequences containing the V161A or V161R mutations.

TABLE 4

Sequences of peptides used in time-course assays

| Immunogenic Region | Wild Type Sequence | Modified Sequences |
|---|---|---|
| R1 | GEWKTQMEETKAQDILGAVTLLLEGVM | GEWKTQKEETKAQDILGAVTLLLEGVM (SEQ ID NO: 129) |
| | | GEWKTQMEERKAQDILGAVTLLLEGVM (SEQ ID NO: 130) |
| | | GEWKTQMEETKRQDILGAVTLLLEGVM (SEQ ID NO: 131) |
| | | GEWKTQMEETKAQRILGAVTLLLEGVM (SEQ ID NO: 132) |
| | | GEWKTQMEETKAQDILGAVTALLEGVM (SEQ ID NO: 133) |
| | | GEWKTQMEETKAQDILGAVTLALEGVM (SEQ ID NO: 134) |
| R2 | PTTAVPSRTSLVLTL | PTTAAPSRTSLVLTL (SEQ ID NO: 135) |
| | | PTTANPSRTSLVLTL (SEQ ID NO: 136) |
| | | PTTARPSRTSLVLTL (SEQ ID NO: 137) |
| | | PTTATPSRTSLVLTL (SEQ ID NO: 138) |

Example 7

Functional Activity of Most Preferred TPO Muteins

Proliferative activity variants of non-immunogenic for both epitope region 1 and epitope region 2 were tested. Supernatants were quantified by Fc ELISA and diluted to 160 ng/ml. The protein activity was titrated in 2 fold serial dilutions and tested in the TF-1 cell proliferation assay. Those changes that gave ≧100% of wild-type activity, and abrogated the T cell proliferative response for both region 1 and region 2, are the most preferred embodiments of the present invention. Relative activity values for all functional muteins are listed in Table 2.

Figure 4:
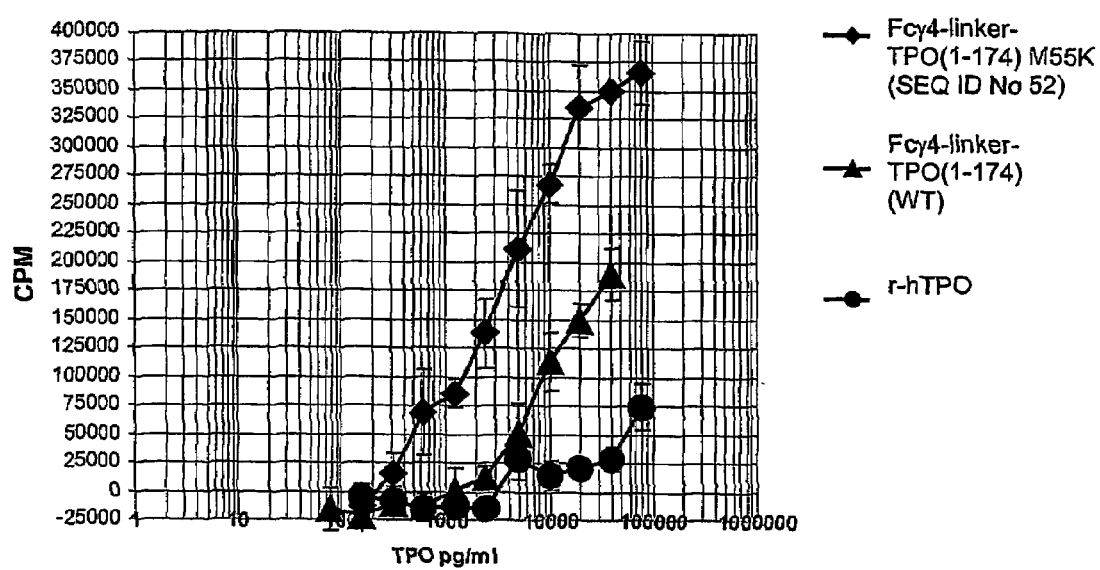

A further preferred TPO mutein is clone ID 102 # (M52/F1-L1-M52) comprising substitution M55K. The M55K substitution was surprisingly shown to produce a beneficial increase in potency of the molecule. This effect is demonstrated in FIG. 4 where the activity in the TF-1 proliferation assay is plotted versus protein concentration. Mutein clone ID # 102 shows significantly greater activity in this functional assay than either the WT counterpart or a control TPO preparation lacking the Fc domain.

Table 5 provides a listing to the relative activites of the most preferred muteins of the invention. The relative activites are derived by dividing the $ED_{50}$ values scored for the test protein by that of the Fc-gamma 4-linked WT TPO (M68/F1-L1-M68). A relative acitivity of 1.0 or less represents a protein with equal or better activity than WT. Values greater than 1.0 indicate inferior activity. The relative activity of the full length WT recombinant human TPO (r-hTPO) is also provided. All values are the average of at least three separate determinations.

TABLE 5

Relative acitivity of most preferred TPO muteins

| Clone ID | F1-L1-M Sequence No | Substitution set | Relative Activity |
|---|---|---|---|
| 37101 | M1 | A60R, V161A | 1 |
| 101102 | M66 | M55K, A60R | 0.2 |
| 37101102 | M67 | M55k, A60R, V161A | 0.4 |
| 102 | M53 | M55K | 0.1 |
| r-hTPO | N/a | WT | 2.5 |

A further example of an especially preferred molecule of the invention with significantly enhanced activity provided by the TPO mutein containing the substititution set M55K, A60R, V161A (M67/F1-L1-M67). This protein is highly potent in the TF-1 assay with relative activity of around 0.4.

Although the M55K, A60R, V161A (M67/F1-L1-M67) mutein is clearly a highly potent molecule, this mutein is not as active as the mutein comprising only the M55K and A60R substitutions (M66/F1-L1-M66). This mutein demonstrates a relative activity of 0.2.

Some of the muteins with two or more substitutions were then tested in the TF-1 and M0-7e proliferation assays. A most preferred protein of the invention Fc-gamma 4-L-TPO (A60R V161A) (M1/F1-L1-M1) was found to retain full activity. The activity of this molecule was compared with both an Fc-gamma 4 linked TPO 1-174 WT molecule (M68/F1-L1-M68), and a preparation of full-length recombinant human (r-hTPO) (PeproTech, London, UK). Results are shown in Table 6.

In TF-1 cells, the native fusion protein, has an $ED_{50}$ of 12.0 ng/ml. In M0-7e cells, the native fusion protein, has an $ED_{50}$ value of 25.0 ng/ml. By contrast, it has been somewhat surprisingly found that a most preferred molecule of the invention (M1/F1-L1-M1) has an $ED_{50}$ value in TF-1 cells of 11.5 ng/ml and in M0-7e cells an $ED_{50}$ value of 18.0 ng/ml. Given that this molecule is a TPO mutein, these results indicate that the changes to the sequence have had a beneficial effect on direct functional activity.

Enhanced potency in the molecule attributed to the dimeric nature of the protein by virtue of the Fc-domain is demonstrated by comparison of the $ED_{50}$ values found using the full size (non-Fc linked) human TPO molecule in TF-1 and E0-7e based proliferation assays (Table 6). Monomeric recombinant human (r-hTPO) TPO achieves an $ED_{50}$ of 29.5 ng/ml using TF-1 cells and 70.0 ng/ml using M0-7e cells. A most preferred molecule of the invention therefore demonstrates approximately between 2.5-4.0 fold enhanced activity over r-hTPO.

Table 6 provides a comparison of the ED50 values scored in both TF-1 and M0-e7 cells; Values shown are for the Fc-gamma 4-linked TPO mutein A60R V161A (M1/F1-L1-M1), the WT Fc-linked counterpart (M68/F1-L1-M68) and a full length WT recombinant human TPO (r-hTPO). Each value is the average of three separate measurements.

TABLE 6

Activities of Fc-gamma 4-linked TPO mutein A60R V161A (M1/F1-L1-M1) with WT TPO Fc-linked counterpart proteins.

| | Proliferation Activity Assay $ED_{50}$ ng/ml | |
|---|---|---|
| Test Protein | TF-1 cells | M0–7e cells |
| Clone ID 37101 - A60R, V161A (M1/F1-L1-M1) | 11.5 | 18.0 |
| Clone ID 00 - WT (M68/F1-L1-M68) | 12.0 | 25.0 |
| r-hTPO | 29.5 | 70.0 |

The invention claimed is:

1. An isolated polypeptide comprising the amino acid residue sequence of SEQ ID NO: 6.

2. A fusion protein comprising a polypeptide of claim 1 linked at the N-terminus thereof to a human immunoglobulin Fc region peptide.

3. The fusion protein of claim 2 wherein the Fc region peptide is linked to the N-terminus of the polypeptide by a linking peptide consisting of the amino acid residue sequence of SEQ ID NO: 5.

4. The fusion protein of claim 2 wherein the Fc region peptide is a human IgG4 Fc region peptide.

5. The fusion protein of claim 4 wherein the human IgG4 Fc region peptide is linked to the N-terminus of the polypeptide by a linking peptide consisting of the amino acid residue sequence of SEQ ID NO: 5.

6. An isolated peptide molecule consisting of SEQ ID NO: 6.

* * * * *